(12) United States Patent
Kadereit et al.

(10) Patent No.: US 8,846,692 B2
(45) Date of Patent: Sep. 30, 2014

(54) CARBOXYLIC ACID DERIVATIVES HAVING A 2,5-SUBSTITUTED OXAZOLOPYRIMIDINE RING

(75) Inventors: Dieter Kadereit, Frankfurt am Main (DE); Matthias Schaefer, Frankfurt am Main (DE); Stephanie Hachtel, Frankfurt am Main (DE); Axel Dietrich, Frankfurt am Main (DE); Thomas Huebschle, Frankfurt am Main (DE); Katrin Hiss, Frankfurt am Main (DE)

(73) Assignee: Sanofi, Paris (FR)

( * ) Notice: Subject to any disclaimer, the term of this patent is extended or adjusted under 35 U.S.C. 154(b) by 242 days.

(21) Appl. No.: 13/521,831

(22) PCT Filed: Jan. 12, 2011

(86) PCT No.: PCT/EP2011/050301
§ 371 (c)(1),
(2), (4) Date: Dec. 10, 2012

(87) PCT Pub. No.: WO2011/086079
PCT Pub. Date: Jul. 21, 2011

(65) Prior Publication Data
US 2013/0079358 A1    Mar. 28, 2013

(30) Foreign Application Priority Data
Jan. 14, 2010    (EP) .................................. 10305042

(51) Int. Cl.
*A01N 43/90*    (2006.01)
*A61K 31/519*   (2006.01)
*C07D 279/00*   (2006.01)
*C07D 498/04*   (2006.01)

(52) U.S. Cl.
CPC .................................. *C07D 498/04* (2013.01)
USPC ....................................... 514/260.1; 544/255

(58) Field of Classification Search
None
See application file for complete search history.

(56) References Cited

FOREIGN PATENT DOCUMENTS

| | | | |
|---|---|---|---|
| WO | WO2004/096813 A1 | 11/2004 |
| WO | WO2005/000833 A1 | 1/2005 |
| WO | WO2010/006704 A1 | 1/2010 |

OTHER PUBLICATIONS

International Search Report dated Feb. 16, 2011 issued in PCT/EP2011/050301.

*Primary Examiner* — Jeffrey H Murray

(57) ABSTRACT

The present invention relates to oxazolopyrimidine compounds of the formula I,

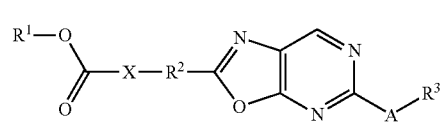

in which A, $R^1$, $R^2$, $R^3$ and X are defined as indicated in the claims. The compounds of the formula I modulate the activity of the Edg-1 receptor and in particular are agonists of this receptor, and are useful for the treatment of diseases such as atherosclerosis, heart failure or peripheral arterial occlusive disease, for example. The invention furthermore relates to processes for the preparation of compounds of the formula I, their use, in particular as active ingredients in pharmaceuticals, and pharmaceutical compositions comprising them.

17 Claims, No Drawings

CARBOXYLIC ACID DERIVATIVES HAVING A 2,5-SUBSTITUTED OXAZOLOPYRIMIDINE RING

The present invention relates to oxazolopyrimidine compounds of the formula I,

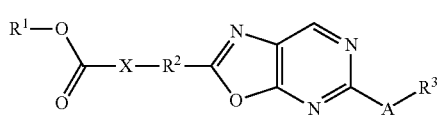

in which A, $R^1$, $R^2$, $R^3$ and X are defined as indicated below. The compounds of the formula I modulate the activity of the Edg-1 receptor and in particular are agonists of this receptor, and are useful for the treatment of diseases such as atherosclerosis, heart failure or peripheral arterial occlusive disease, for example. The invention furthermore relates to processes for the preparation of compounds of the formula I, their use, in particular as active ingredients in pharmaceuticals, and pharmaceutical compositions comprising them.

The Edg-1 receptor is a member of the endothelial differentiation gene (Edg) receptor family of currently eight identified class A GPCRs (G-protein coupled receptors). This family can be divided into subfamilies of sphingosine-1-phosphate (S1P)-activated receptors (five members) and receptors activated by lysophosphatidic acid (LPA; three members). The endogenous ligand S1P is a pluripotent lysophospholipid acting on different cell types by activating GPCRs from the Edg receptor family, namely Edg-1 (=S1P1), Edg-3 (=S1P3), Edg-5 (=S1P2), Edg-6 (=S1P4) and Edg-8 (S1P5). Although formerly S1P was also described as an intracellular messenger, there is increasing evidence in the literature that most effects of S1P are mediated Edg receptor-dependent. S1P is generated by the enzyme family of sphingosine kinases (SPHK) and degraded by different phosphatases or lyases (for an overview, see D. Meyer zu Heringdorf et al., Biochim. Biophys. Acta 1768 (2007), 923-940). Regarding the vasculature, it is evident that the Edg-1 receptor is prominently expressed in endothelial cells, whereas it is only slightly expressed in vascular smooth muscle cells in which Edg-3 and Edg-5 are the predominant S1P receptors. Thus, the differential expression of S1P receptors in the vasculature makes specific Edg-1 receptor activation desirable, since in contrast to the endogenous ligand S1P it leads to pronounced endothelial activation without having relevant effects on vascular smooth muscle cells. Activation of Edg-1 receptor in endothelial cells was shown to be beneficial in respect to endothelial cell function in the context of atherosclerosis (for an overview, see H. Ozaki, et al., J. Atheroscler. Thromb. 10 (2003), 125-131). Edg-1 signalling was formerly shown to lead to liberation of nitric oxide (=NO) (J. Igarashi et al., J. Biol. Chem. 275 (2000), 32363-32370) and to preserve its anti-adhesive features, since it prevents from cytokine-induced cell-adhesion molecule exposure and monocyte adhesion to endothelial cells (D. T. Bolick et al., Arterioscler. Thromb. Vasc. Biol. 25 (2005), 976-981). Furthermore, Edg-1 receptor signalling promotes endothelial cell migration and endothelial cell survival (Y.-G. Kwon et al., J. Biol. Chem. 276 (2001), 10627-10633). A specific feature of Edg-1 receptor signalling is the protection of the endothelial cell barrier function by targeting reorganization of actin fibers and proteins critical for the stabilization of adherens junctions such as N-cadherin (J.-H. Paik et al., Genes Develop. 18 (2004), 2392-2403), enforcing cell-cell contacts and thus leading to decreased paracellular permeability of the endothelium (K. L. Schaphorst et al., Am. J. Physiol. Lung Cell. Mol. Physiol. 285 (2003), L258-L267). Although it has no effect on the development of vessel network itself, Edg-1 receptor signalling is essential for vascular maturation, where it promotes stabilization of nascend vessels. Edg-1 receptor knock-out mice are not viable and die from intra-uterinic hemorrhages, since signalling is non-redundant during embryonic angiogenesis (M. Kono et al., J. Biol. Chem. 279 (2004), 29367-29373). The relevance of Edg-1 signalling for vascular maturation is obvious also with respect to tumor vascularization, since pharmacological impairment of Edg-1 signalling is anti-angiogenic and critical for tumor vascularization (K. LaMontagne et al., Cancer Res. 66 (2006), 221-231), as has been demonstrated also by an in vivo siRNA approach targeting the Edg-1 receptor (S.-S. Chae et al., J. Clin. Invest. 114 (2004), 1082-1089). Recently, it was demonstrated that signalling of the Edg-5 receptor, which is also expressed in endothelial cells to a lower extent, opposes the protective Edg-1 effects regarding reduction of vascular permeability (T. Sanchez et al., Arterioscler. Thromb. Vasc. Bio. 27 (2007), 1312-1318), underlining again the need for specific Edg-1 agonists in order to improve endothelial function.

Key indications of Edg-1 receptor agonists include cardiovascular diseases, atherosclerosis, heart failure, cardio protection, peripheral arterial occlusive disease, renal diseases, inflammatory diseases, vascular permeability disorders, diabetes, respiratory diseases and cytoprotection, for example. Edg-1 agonists can also be used in higher dosages to lead to a functional impairment of Edg-1 receptor signalling due to tachyphylaxis/receptor desensitization. This offers the opportunity to use Edg-1 receptor agonists also as immunosuppressants and for the treatment of multiple sclerosis or cancer. The use for immunosuppression and for the treatment of multiple sclerosis has been investigated for the unselective Edg-1 receptor agonist FTY-720 (fingolimod) which is currently in phase III clinical studies for the treatment of multiple sclerosis. The use of FTY-720 for the prevention of atherosclerosis has been recently shown in two independent investigations (see J.-R. Nofer et al., Circulation 115 (2007), 501-508; P. Keul et al., Arterioscler. Thromb. Vasc. Biol. 27 (2007), 607-613). Edg-1 agonists can also be used in combination with other pharmacologically active compounds, for example with cytostatic agents in which case the Edg-1 agonist provides for endothelial cell protection, or with antiatherosclerotic agents such as statins or HDL (high density lipoprotein) enhancers. Additionally, Edg-1 agonists can be used in combination with pharmacologically active compounds which may generate edema as side effect, for example PPARgamma (peroxisome proliferator-activated receptor gamma) agonists, ACE/NEP (angiotensin converting enzyme/neutral endopeptidase) inhibitors or factor Xa inhibitors, or in the treatment of septic shock. Furthermore, Edg-1 agonists can be used for preventing vascular hyperpermeability as seen, for example, during cardiac surgery.

Several classes of low molecular weight Edg-1 agonists have been described in the prior art, for example in WO 03/061567, WO 2005/000833, WO 2005/058848, WO 2005/123677, WO 2006/010379 and WO 2006/047195. However, there continues to be a need for further effective low molecular weight Edg-1 agonists, in particular in view of safety and Edg receptor selectivity. In addition, besides being effective as Edg-1 agonists, it is desirable that such compounds also have further advantageous properties, for example stability in plasma, liver and vascular tissue. The present invention satisfies this need by providing the oxazolopyrimidine compounds of the formula I which are unsubstituted in position 7 of the oxazolopyrimidine ring system.

Bicyclic pyrimidine derivatives which are useful for pharmaceutical applications, have already been disclosed, for example in EP 1666468, WO 2004/096813, WO 2005/067546, and WO 2005/069865. However, the oxazolo[5,4-d]pyrimidine compounds of the formula I have not yet been mentioned, and the use of such compounds as Edg-1 agonists is not suggested by the prior art.

A subject of the present invention is an oxazolopyrimidine compound of the formula I, in any of its stereoisomeric forms, or a mixture of stereoisomeric forms in any ratio, or a physiologically acceptable salt thereof, or a physiologically acceptable solvate of any of them,

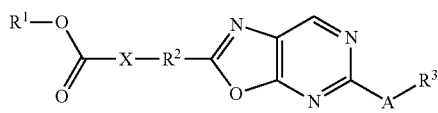

wherein
A is chosen from NH, O and S;
X is chosen from ($C_1$-$C_6$)-alkanediyl, ($C_2$-$C_6$)-alkenediyl, ($C_2$-$C_6$)-alkynediyl, ($C_3$-$C_7$)-cycloalkanediyl and ($C_1$-$C_6$)-alkanediyl-oxy, which all are optionally substituted by one or more identical or different substituents chosen from fluorine and hydroxy, wherein the oxygen atom of the ($C_1$-$C_6$)-alkanediyl-oxy group is bonded to the group $R^2$;
$R^1$ is chosen from hydrogen, ($C_1$-$C_4$)-alkyl and ($C_3$-$C_7$)-cycloalkyl-$C_zH_{2z}$—, wherein z is chosen from 0, 1 and 2;
$R^2$ is chosen from phenylene and a divalent residue of an aromatic, 5-membered to 6-membered monocyclic heterocycle which comprises 1, 2 or 3 identical or different ring heteroatoms chosen from N, O and S, wherein one of the ring nitrogen atoms can carry a hydrogen atom or a substituent $R^{21}$, and wherein the phenylene and divalent residue of an aromatic heterocycle are optionally substituted on one or more ring carbon atoms by identical or different substituents $R^{22}$;
$R^3$ is chosen from ($C_1$-$C_6$)-alkyl, ($C_2$-$C_6$)-alkenyl, ($C_2$-$C_6$)-alkynyl, ($C_3$-$C_7$)-cycloalkyl-$C_uH_{2u}$— and Het-$C_vH_{2v}$—, wherein u and v are chosen from 1 and 2, or $R^3$ is a residue of a saturated or unsaturated, 3-membered to 10-membered, monocyclic or bicyclic ring which comprises 0, 1, 2, 3 or 4 identical or different ring heteroatoms chosen from N, O and S, wherein one or two of the ring nitrogen atoms can carry a hydrogen atom or a ($C_1$-$C_4$)-alkyl substituent and one or two of the ring sulfur atoms can carry one or two oxo groups, and wherein the residue of a ring is optionally substituted on one or more ring carbon atoms by identical or different substituents $R^{31}$;
$R^{21}$ is chosen from ($C_1$-$C_4$)-alkyl, ($C_3$-$C_7$)-cycloalkyl-$C_wH_{2w}$— and oxy, wherein w is chosen from 0, 1 and 2;
$R^{22}$ is chosen from halogen, hydroxy, ($C_1$-$C_4$)-alkyl-, ($C_1$-$C_4$)-alkyloxy, ($C_1$-$C_4$)-alkyl-S(O)$_m$—, amino, nitro, cyano, hydroxycarbonyl, ($C_1$-$C_4$)-alkyloxycarbonyl, aminocarbonyl and aminosulfonyl;
$R^{31}$ is chosen from halogen, ($C_1$-$C_4$)-alkyl, ($C_3$-$C_7$)-cycloalkyl, hydroxy, ($C_1$-$C_4$)-alkyloxy, oxo, ($C_1$-$C_4$)-alkyl-S(O)$_m$—, amino, ($C_1$-$C_4$)-alkylamino, di(($C_1$-$C_4$)-alkyl)amino, ($C_1$-$C_4$)-alkylcarbonylamino, ($C_1$-$C_4$)-alkylsulfonylamino, nitro, cyano, ($C_1$-$C_4$)-alkylcarbonyl, aminosulfonyl, ($C_1$-$C_4$)-alkylaminosulfonyl and di(($C_1$-$C_4$)-alkyl)aminosulfonyl;

Het is a residue of a saturated, 4-membered to 7-membered, monocyclic heterocycle which comprises 1 or 2 identical or different ring heteroatoms chosen from N, O and S and which is bonded via a ring carbon atom, wherein the residue of a heterocycle is optionally substituted by one or more identical or different substituents chosen from fluorine and ($C_1$-$C_4$)-alkyl;
m is chosen from 0, 1 and 2, wherein all numbers m are independent of each other;
wherein all cycloalkyl and cycloalkanediyl groups, independently of each other and independently of any other substituents, are optionally substituted by one or more identical or different substituents chosen from fluorine and ($C_1$-$C_4$)-alkyl;
wherein all alkyl, alkanediyl, $C_uH_{2u}$, $C_vH_{2v}$, $C_wH_{2w}$, $C_zH_{2z}$, alkenyl, alkenediyl, alkynyl and alkynediyl groups, independently of each other and independently of any other substituents, are optionally substituted by one or more fluorine substituents.

Structural elements such as groups, substituents, hetero ring members, numbers or other features, for example alkyl groups, groups like $R^{22}$ or $R^{31}$, numbers like m, u and v, which can occur several times in the compounds of the formula I, can all independently of one another have any of the indicated meanings and can in each case be identical to or different from one another. For example, the alkyl groups in a dialkylamino group can be identical or different.

Alkyl, alkenyl and alkynyl groups can be linear, i.e. straight-chain, or branched. This also applies when they are part of other groups, for example alkyloxy groups (=alkoxy groups, alkyl-O— groups), alkyloxycarbonyl groups or alkyl-substituted amino groups, or when they are substituted. Depending on the respective definition, the number of carbon atoms in an alkyl group can be 1, 2, 3, 4, 5 or 6, or 1, 2, 3 or 4, or 1, 2 or 3. Examples of alkyl are methyl, ethyl, propyl including n-propyl and isopropyl, butyl including n-butyl, sec-butyl, isobutyl and tert-butyl, pentyl including n-pentyl, 1-methylbutyl, isopentyl, neopentyl and tert-pentyl, and hexyl including n-hexyl, 3,3-dimethylbutyl and isohexyl. Double bonds and triple bonds in alkenyl groups and alkynyl groups can be present in any positions. In one embodiment of the invention, alkenyl groups contain one double bond and alkynyl groups contain one triple bond. In one embodiment of the invention, an alkenyl group or alkynyl group contains at least three carbon atoms and is bonded to the remainder of the molecule via a carbon atom which is not part of a double bond or triple bond. Examples of alkenyl and alkynyl are ethenyl, prop-1-enyl, prop-2-enyl (=allyl), but-2-enyl, 2-methylprop-2-enyl, 3-methylbut-2-enyl, hex-3-enyl, hex-4-enyl, prop-2-ynyl (=propargyl), but-2-ynyl, but-3-ynyl, hex-4-ynyl or hex-5-ynyl. Substituted alkyl groups, alkenyl groups and alkynyl groups can be substituted in any positions, provided that the respective compound is sufficiently stable and is suitable for the desired purpose such as use as a drug substance. The prerequisite that a specific group and a compound of the formula I are sufficiently stable and suitable for the desired purpose such as use as a drug substance, applies in general with respect to the definitions of all groups in the compounds of the formula I.

As far as applicable, the preceding explanations regarding alkyl, alkenyl and alkynyl groups apply correspondingly to divalent alkyl groups such as the groups alkanediyl, $C_uH_{2u}$, $C_vH_{2v}$, $C_wH_{2w}$ and $C_zH_{2z}$ and divalent alkenyl groups and alkynyl groups such as the groups alkenediyl and alkynediyl, which thus can likewise be linear and branched. The double bonds and triple bonds in alkenediyl and alkynediyl groups can be present in any positions. In one embodiment of the invention, alkenediyl groups contain one double bond and alkynediyl groups contain one triple bond. Examples of divalent alkyl groups are —CH$_2$— (=methylene), —CH$_2$—CH$_2$—, —CH$_2$—CH$_2$—CH$_2$—, —CH$_2$—CH$_2$—CH$_2$—CH$_2$—, —CH(CH$_3$)—, —C(CH$_3$)$_2$—, —CH(CH$_3$)—CH$_2$—, —CH$_2$—CH(CH$_3$)—, —C(CH$_3$)$_2$—CH$_2$—, —CH$_2$—C(CH$_3$)$_2$—, examples of divalent alkenyl groups are —CH=CH—, —CH$_2$—CH=CH—, —CH=CH—CH$_2$—, —CH$_2$—CH=CH—CH$_2$—, —CH$_2$—CH$_2$—CH=CH—, —C(CH$_3$)=C(CH$_3$)—, and examples of divalent alkynyl groups are —C≡C—, —CH$_2$—C≡C—, —C≡C—CH$_2$—, —C(CH$_3$)$_2$—C≡C—, —C≡C—C(CH$_3$)$_2$—, —CH$_2$—C≡C—CH$_2$—, —CH$_2$—CH$_2$—C≡C—. If a number in a divalent group such as the number z in the group C$_z$H$_{2z}$, for example, is 0 (=zero), the two groups which are attached to the contemplated group, such as C$_z$H$_{2z}$, are directly connected to one another via a single bond.

The number of ring carbon atoms in a cycloalkyl group can be 3, 4, 5, 6 or 7. In one embodiment of the invention, the number of ring carbon atoms in a cycloalkyl group, independently of the number of ring carbon atoms in any other cycloalkyl group, is 3, 4, 5 or 6, in another embodiment 3, 4 or 5, in another embodiment 3 or 4, in another embodiment 3, in another embodiment 5, 6 or 7, in another embodiment 5 or 6, in another embodiment 6 or 7, in another embodiment 6. This applies accordingly to divalent cycloalkyl groups, i.e. cycloalkanediyl groups, which can be bonded to the adjacent groups via any one or two ring carbon atoms. Examples of cycloalkyl groups are cyclopropyl, cyclobutyl, cyclopentyl, cyclohexyl and cycloheptyl. Examples of divalent cycloalkyl groups are cyclopropane-1,1-diyl, cyclopropane-1,2-diyl, cyclobutane-1,3-diyl, cyclopentane-1,1-diyl, cyclopentane-1,2-diyl, cyclopentane-1,3-diyl, cyclohexane-1,1-diyl, cyclohexane-1,2-diyl, cyclohexane-1,3-diyl, cyclohexane-1,4-diyl, cycloheptane-1,4-diyl. Independently of one another and independently of any other substituents, cycloalkyl groups and cycloalkanediyl groups are optionally substituted by one or more identical or different (C$_1$-C$_4$)-alkyl substituents which can be located in any positions, i.e., cycloalkyl groups can be unsubstituted by alkyl substituents or substituted by alkyl substituents, for example by 1, 2, 3 or 4, or by 1 or 2, (C$_1$-C$_4$)-alkyl substituents, for example by methyl groups. Examples of alkyl-substituted cycloalkyl groups and cycloalkanediyl groups are 4-methylcyclohexyl, 4-tert-butylcyclohexyl or 2,3-dimethylcyclopentyl, 2,2-dimethylcyclopropane-1,1-diyl, 2,2-dimethylcyclopropane-1,2-diyl, 2,2-dimethylcylopentane-1,3-diyl, 6,6-dimethylcycloheptane-1,4-diyl. Examples of cycloalkylalkyl groups, which can represent groups such as (C$_3$-C$_7$)-cycloalkyl-C$_z$H$_{2z}$—, for example, are cyclopropylmethyl, cyclobutylmethyl, cyclopentylmethyl, cyclohexylmethyl, cycloheptylmethyl, 1-cyclopropylethyl, 2-cyclopropylethyl, 1-cyclobutylethyl, 2-cyclobutylethyl, 2-cyclopentylethyl, 2-cyclohexylethyl, 2-cycloheptylethyl.

Independently of one another and independently of any other substituents, alkyl groups, divalent alkyl groups, alkenyl groups, divalent alkenyl groups, alkynyl groups, divalent alkynyl groups, cycloalkyl groups and divalent cycloalkyl groups are optionally substituted by one or more fluorine substituents which can be located in any positions, i.e., the said groups can be unsubstituted by fluorine substituents or substituted by fluorine substituents, for example by 1, 2, 3, 4, 5, 6, 7, 8, 9, 10, 11, 12 or 13, or by 1, 2, 3, 4, 5, 6, 7, 8 or 9, or by 1, 2, 3, 4, 5, 6 or 7, or by 1, 2, 3, 4 or 5, or by 1, 2 or 3, or by 1 or 2, fluorine substituents. Examples of fluorine-substituted said groups are trifluoromethyl, 2-fluoroethyl, 2,2,2-trifluoroethyl, pentafluoroethyl, 3,3,3-trifluoropropyl, 2,2,3,3,3-pentafluoropropyl, 4,4,4-trifluorobutyl, heptafluoroisopropyl, —CHF—, —CF$_2$—, —CF$_2$—CH$_2$—, —CH$_2$—CF$_2$—, —CF$_2$—CF$_2$—, —CF(CH$_3$)—, —C(CF$_3$)$_2$—, 1-fluorocyclopropyl, 2,2-difluorocyclopropyl, 3,3-difluorocyclobutyl, 1-fluorocyclohexyl, 4,4-difluorocyclohexyl, 3,3,4,4,5,5-hexafluorocyclohexyl, 2,2-difluorocyclopropane-1,2-diyl. Examples of alkyloxy groups in which the alkyl moiety is fluorine-substituted, are trifluoromethoxy, 2,2,2-trifluoroethoxy, pentafluoroethoxy and 3,3,3-trifluoropropoxy. In one embodiment of the invention, the total number of fluorine substituents and (C$_1$-C$_4$)-alkyl substituents, which independently of any other substituents are optionally present on cycloalkyl groups and cycloalkanediyl groups in the compounds of the formula I, is 1, 2, 3, 4, 5, 6, 7, 8, 9, 10 or 11, in another embodiment 1, 2, 3, 4, 5, 6, 7, 8 or 9, in another embodiment 1, 2, 3, 4 or 5, in another embodiment 1, 2, 3 or 4.

Groups like phenyl, naphthyl (=naphthalenyl) and residues of aromatic heterocycles which are optionally substituted by one or more substituents, can be unsubstituted or substituted, for example by 1, 2, 3, 4 or 5, or by 1, 2, 3 or 4, or by 1, 2 or 3, or by 1 or 2, or by 1, identical or different substituents which can be located in any positions. In one embodiment of the invention the total number of nitro substituents in a compound of the formula I is not greater than two. Aromatic nitrogen heterocycles which in the parent ring system carry a hydrogen atom on a ring nitrogen atom in a 5-membered ring, such as a pyrrole, imidazole, indole or benzoimidazole ring, for example, can be substituted on ring carbon atoms and/or on such ring nitrogen atoms. In one embodiment of the invention, substituents on such ring nitrogen atoms are chosen from (C$_1$-C$_4$)-alkyl groups, i.e. such ring nitrogen atoms in aromatic heterocycles carry a hydrogen atom or a (C$_1$-C$_4$)-alkyl substituent. When it is stated with respect to ring nitrogen atoms in aromatic heterocycles and any other heterocycles that they can carry a hydrogen atom or a substituent, such ring nitrogen atoms either carry a hydrogen atom or a substituent, or they do not carry a hydrogen atom or substituent. Ring nitrogen atoms which carry a hydrogen atom or a substituent, occur in a nitrogen-containing aromatic 5-membered ring as is present in pyrrole, imidazole, indole or benzoimidazole, for example, and in a non-aromatic ring including a saturated ring. Ring nitrogen atoms which do not carry a hydrogen atom or a substituent unless they are present in positively charged form, including any further ring nitrogen atoms in addition to ring nitrogen atoms which carry a hydrogen atom or a substituent, occur in an aromatic ring as is present in thiazole, imidazole, pyridine or benzoimidazole, for example, and in a non-aromatic ring in which they are bridgehead atoms or are part of a double bond, and they occur as ring nitrogen atoms via which a ring is bonded. Suitable ring nitrogen atoms in aromatic heterocycles in the compounds of the formula I, such as the ring nitrogen atom in a pyridine ring, specifically a ring nitrogen atom in an aromatic heterocycle representing R$^2$, can also carry an oxy substituent —O$^-$ and be present as an N-oxide, and such ring nitrogen atoms can also be present as quaternary salt, for example as N—(C$_1$-C$_4$)-alkyl salt such as N-methyl salt, wherein in one embodiment of the invention the counter anion in such quaternary salt is a physiologically acceptable anion which is derived from an acid that forms a physiologically acceptable salt. In monosubstituted phenyl groups, the substituent can be located in the 2-position, the 3-position or the 4-position. In disubstituted phenyl groups, the substituents can be located in 2,3-position, 2,4-position, 2,5-position, 2,6-position, 3,4-position or 3,5-position. In trisubstituted phenyl groups, the substituents can be located in 2,3,4-position, 2,3,5-position, 2,3,6-position, 2,4,5-position, 2,4,6-position or 3,4,5-position. Naphthyl can be 1-naphthyl (=naphthalen-1-yl) or 2-naphthyl (=naphthalen-2-yl). In monosubstituted 1-naphthyl groups, the substituent can be located in the 2-, 3-, 4-, 5-, 6-, 7- or 8-position. In monosubstituted 2-naphthyl groups, the substituent can be located in the 1-, 3-, 4-, 5-, 6-, 7- or 8-position. In disubstituted naphthyl groups, the substituents can likewise be located in any positions both in the ring via which the naphthyl group is bonded and/or in the other ring. These statement relating to the monovalent residues apply accordingly to the respective divalent residues, such as phenylene groups representing $R^2$, for example, which thus can likewise be unsubstituted or substituted, for example by 1, 2, 3 or 4, or by 1, 2 or 3, or by 1 or 2, or by 1, identical or different substituents which can be located in any positions.

In residues of aromatic heterocycles representing $R^2$ or $R^3$, which may be designated as heteroaryl and heteroarylene groups, as well as in all other heterocyclic rings in the compounds of the formula I including the group Het and non-aromatic heterocyclic groups representing $R^3$, the ring heteroatoms are generally chosen from N, O and S, wherein N includes ring nitrogen atoms which carry a hydrogen atom or a substituent as well as ring nitrogen atom which do not carry a hydrogen atom or a substituent. Ring heteroatoms can be located in any positions, provided that the heterocyclic system is known in the art and is stable and suitable as a subgroup for the desired purpose of the compound of the formula I such as use as a drug substance. In one embodiment of the invention, two ring oxygen atoms cannot be present in adjacent ring positions of any heterocycle, in another embodiment two ring heteroatoms chosen from oxygen and sulfur cannot be present in adjacent ring positions of any heterocycle. Saturated rings do not contain a double bond within the ring. Unsaturated ring systems can be aromatic or partially unsaturated including partially aromatic, in which latter case one ring in a bicyclic ring system is aromatic and the ring system is bonded via an atom in the non-aromatic ring. Depending on the respective group, unsaturated rings can contain one, two, three, four or five double bonds within the ring. Aromatic groups contain a cyclic system of six or ten delocalized pi electrons in the ring. Depending on the respective group, saturated and non-aromatic unsaturated heterocyclic rings, including Het and non-aromatic groups representing $R^3$, can be 3-membered, 4-membered, 5-membered, 6-membered, 7-membered, 8-membered, 9-membered or 10-membered. In one embodiment of the invention, aromatic heterocyclic rings are 5-membered or 6-membered monocyclic rings or 8-membered, 9-membered or 10-membered bicyclic rings, in another embodiment 5-membered or 6-membered monocyclic rings or 9-membered or 10-membered bicyclic rings, in another embodiment 5-membered or 6-membered monocyclic rings, wherein the 8-membered, 9-membered or 10-membered bicyclic rings are composed of two fused 5-membered rings, a 5-membered ring and a 6-membered ring which are fused to one another, and two fused 6-membered rings, respectively. In bicyclic aromatic heterocyclic groups, one or both rings can contain hetero ring members, and one or both rings can be aromatic. In general, bicyclic ring systems containing an aromatic ring and a non-aromatic ring are regarded as aromatic when they are bonded via a carbon atom in the aromatic ring, and as non-aromatic when they are bonded via a carbon atom in the non-aromatic ring. Unless stated otherwise, heterocyclic groups including aromatic heterocyclic groups can be bonded via any suitable ring carbon atom and, in the case of nitrogen heterocycles, via any suitable ring nitrogen atom. In one embodiment of the invention, an aromatic heterocyclic group in a compound of the formula I, independently of any other aromatic heterocyclic group, is bonded via a ring carbon atom, in another embodiment via a ring nitrogen atom. Depending on the definition of the respective heterocyclic group, in one embodiment of the invention the number of ring heteroatoms which can be present in a heterocyclic group, independently of the number of ring heteroatoms in any other heterocyclic group, is 1, 2, 3 or 4, in another embodiment 1, 2 or 3, in another embodiment 1 or 2, in another embodiment 1, wherein the ring heteroatoms can be identical or different. Heterocyclic groups which are optionally substituted, can independently of any other heterocyclic group be unsubstituted or substituted by one or more identical or different substituents, for example by 1, 2, 3, 4 or 5, or by 1, 2, 3 or 4, or by 1, 2 or 3, or by 1 or 2, or by 1 substituents, which are indicated in the definition of the respective group. Substituents on heterocyclic groups can be located in any positions. For example, in a pyridin-2-yl group substituents can be located in the 3-position and/or 4-position and/or 5-position and/or 6-position, in a pyridin-3-yl group substituent can be located in the 2-position and/or 4-position and/or 5-position and/or 6-position, in a pyridin-4-yl group substituents can be located in the 2-position and/or 3-position and/or 5-position and/or 6-position.

Examples of parent heterocycles, from which heterocyclic groups including aromatic heterocyclic groups, saturated heterocyclic groups and non-aromatic unsaturated heterocyclic groups can be derived, are azete, oxete, pyrrole, furan, thiophene, imidazole, pyrazole, [1,3]dioxole, oxazole (=[1,3]oxazole), isoxazole (=[1,2]oxazole), thiazole (=[1,3]thiazole), isothiazole (=[1,2]thiazole), [1,2,3]triazole, [1,2,4]triazole, [1,2,4]oxadiazole, [1,3,4]oxadiazole, [1,2,4]thiadiazole, [1,3,4]thiadiazole, tetrazole, pyridine, pyran, thiopyran, pyridazine, pyrimidine, pyrazine, [1,3]oxazine, [1,4]oxazine, [1,3]thiazine, [1,4]thiazine, [1,2,3]triazine, [1,3]dithiine, [1,4]dithiine, [1,2,4]triazine, [1,3,5]triazine, [1,2,4,5]tetrazine, azepine, [1,3]diazepine, [1,4]diazepine, [1,3]oxazepine, [1,4]oxazepine, [1,3]thiazepine, [1,4]thiazepine, azocine, azecine, cyclopenta[b]pyrrole, 2-azabicyclo[3.1.0]hexane, 3-azabicyclo[3.1.0]hexane, 2-oxa-5-azabicyclo[2.2.1]heptane, indole, isoindole, benzothiophene, benzofuran, [1,3]benzodioxole (=1,2-methylenedioxybenzene), [1,3]benzoxazole, [1,3]benzothiazole, benzoimidazole, thieno[3,2-c]pyridine, chromene, isochromene, [1,4]benzodioxine, [1,4]benzoxazine, [1,4]benzothiazine, quinoline, isoquinoline, cinnoline, quinazoline, quinoxaline, phthalazine, thienothiophenes, [1,8]naphthyridine and other naphthyridines, pteridine, and the respective saturated and partially unsaturated heterocycles in which one or more, for example one, two, three, four or all double bonds within the ring system including double bonds in aromatic ring are replaced with single bonds, such as azetidine, oxetane, pyrrolidine, tetrahydrofuran, tetrahydrothiophene, imidazolidine, oxazolidine, thiazolidine, dihydropyridine, piperidine, tetrahydropyran, piperazine, morpholine, thiomorpholine, azepane, chroman, isochroman, [1,4]benzodioxane (=1,2-ethylenedioxybenzene), 2,3-dihydrobenzofuran, 1,2,3,4-tetrahydroquinoline, 1,2,3,4-tetrahydroisoquinoline, for example.

Examples of residues of aromatic heterocycles, which can occur in the compounds of the formula I, are thiophenyl (=thienyl) including thiophen-2-yl and thiophen-3-yl, pyridinyl (=pyridyl) including pyridin-2-yl (=2-pyridyl), pyridin-3-yl (=3-pyridyl) and pyridin-4-yl (=4-pyridyl), imidazolyl including, for example, 1H-imidazol-1-yl, 1H-imidazol-2-yl, 1H-imidazol-4-yl and 1H-imidazol-5-yl, [1,2,4]triazolyl including 1H-[1,2,4]-triazol-1-yl and 4H-[1,2,4-triazol-3-yl, tetrazolyl including 1H-tetrazol-1-yl and 1H-tetrazol-5-yl, quinolinyl (=quinolyl) including quinolin-2-yl, quinolin-3-yl, quinolin-4-yl, quinolin-5-yl, quinolin-6-yl, quinolin-7-yl and quinolin-8-yl, which all are optionally substituted as indicated in the definition of the respective group. Examples of residues of saturated and partially unsaturated heterocycles, which can occur in the compounds of the formula I, are azetidinyl, pyrrolidinyl including pyrrolidin-1-yl, pyrrolidin-2-yl and pyrrolidin-3-yl, 2,5-dihydro-1H-pyrrolyl, piperidinyl including piperidin-1-yl, piperidin-2-yl, piperidin-3-yl and piperidin-4-yl, 1,2,3,4-tetrahydropyridinyl, 1,2,5,6-tetrahydropyridinyl, 1,2-dihydropyridinyl, azepanyl, azocanyl, azecanyl, octahydrocyclopenta[b]pyrrolyl, 2,3-dihydrobenzofuranyl including 2,3-dihydrobenzofuran-7-yl, 2,3-dihydro-1H-indolyl, octahydro-1H-indolyl, 2,3-dihydro-1H-isoindolyl, octahydro-1H-isoindolyl, 1,2-dihydroquinolinyl, 1,2,3,4-tetrahydroquinolinyl, decahydroquinolinyl, 1,2-dihydroisoquinolinyl, 1,2,3,4-tetrahydroisoquinolinyl, 1,2,3,4-tetrahydroisoquinolinyl, decahydroisoquinolinyl, decahydroisoquinolinyl, 4,5,6,7-tetrahydrothieno[3,2-c]pyridinyl, pyrazolidinyl, imidazolidinyl, hexahydropyrimidinyl, 1,2-dihydropyrimidinyl, piperazinyl, [1,3]diazepanyl, [1,4]diazepanyl, oxazolidinyl, [1,3]oxazinanyl, [1,3]oxazepanyl, morpholinyl including morpholin-2-yl, morpholin-3-yl and morpholin-4-yl, [1,4]oxazepanyl, thiazolidinyl, [1,3]thiazinanyl, thiomorpholinyl including thiomorpholin-2-yl, thiomorpholin-3-yl and thiomorpholin-4-yl, 3,4-dihydro-2H-[1,4]thiazinyl, [1,3]thiazepanyl, [1,4]thiazepanyl, [1,4]thiazepanyl, oxetanyl, tetrahydrofuranyl, tetrahydrothienyl, isoxazolidinyl, isothiazolidinyl, oxazolidinyl, [1,2,4]-oxadiazolidinyl, [1,2,4]-thiadiazolidinyl, [1,2,4]triazolidinyl, [1,3,4]oxadiazolidinyl, [1,3,4]thiadiazol idinyl, [1,3,4]triazolidinyl, 2,3-dihydrofuranyl, 2,5-dihydrofuranyl, 2,3-dihydrothienyl, 2,5-dihydrothienyl, 2,3-dihydropyrrolyl, 2,3-dihydroisoxazolyl, 4,5-dihydroisoxazolyl, 2,5-dihydroisoxazolyl, 2,3-dihydroisothiazolyl, 4,5-dihydroisothiazolyl, 2,5-dihydroisothiazolyl, 2,3-dihydropyrazolyl, 4,5-dihydropyrazolyl, 2,5-dihydropyrazolyl, 2,3-dihydrooxazolyl, 4,5-dihydrooxazolyl, 2,5-dihydrooxazolyl, 2,3-dihydrothiazolyl, 4,5-dihydrothiazolyl, 2,5-dihydrothiazolyl, 2,3-dihydroimidazolyl, 4,5-dihydroimidazolyl, 2,5-dihydroimidazolyl, tetrahydropyridazinyl, tetrahydropyrimidinyl, tetrahydropyrazinyl, tetrahydro[1,3,5]triazinyl, [1,3]dithianyl, tetrahydropyranyl, tetrahydrothiopyranyl, [1,3]dioxolanyl, 3,4,5,6-tetrahydropyridinyl, 4H-[1,3]thiazinyl, 1,1-dioxo-2,3,4,5-tetrahydrothienyl, 2-azabicyclo[3.1.0] hexyl including 2-azabicyclo[3.1.0]hex-2-yl, 3-azabicyclo [3.1.0]hexyl including 3-azabicyclo[3.1.0]hex-3-yl, 2-oxa-5-azabicyclo[2.2.1]-heptyl including 2-oxa-5-azabicyclo [2.2.1]-hept-5-yl, which all are bonded via any suitable ring carbon atom or ring nitrogen atom and are optionally substituted as indicated in the definition of the respective group.

Halogen is fluorine, chlorine, bromine or iodine. In one embodiment of the invention, any halogen in a compound of the formula I is independently of any other halogen chosen from fluorine, chlorine and bromine, in another embodiment from fluorine and chlorine.

When an oxo group is bonded to a carbon atom, it replaces two hydrogen atoms on a carbon atom of the parent system. Thus, if a $CH_2$ group in a chain or a ring is substituted by oxo, i.e. by a doubly bonded oxygen atom, it becomes a C(O) (=C(=O)) group. Evidently, an oxo group cannot occur as a substituent on a carbon atom in an aromatic ring such as in a phenyl group, for example. When a ring sulfur atom in a heterocyclic group can carry one or two oxo groups, it is a non-oxidized sulfur atom S in case it does not carry any oxo group, or it is an S(O) group (=sulfoxide group, S-oxide group) in case it carries one oxo group, or it is an $S(O)_2$ group (=sulfone group, S,S-dioxide group) in case it carries two oxo groups.

The present invention includes all stereoisomeric forms of the compounds of the formula I and their salts and solvates. With respect to each chiral center, independently of any other chiral center, the compounds of the formula I can be present in S configuration or substantially S configuration, or in R configuration or substantially R configuration, or as a mixture of the S isomer and the R isomer in any ratio. The invention includes all possible enantiomers and diastereomers and mixtures of two or more stereoisomers, for example mixtures of enantiomers and/or diastereomers, in all ratios. Thus, compounds according to the invention which can exist as enantiomers can be present in enantiomerically pure form, both as levorotatory and as dextrorotatory antipodes, and in the form of mixtures of the two enantiomers in all ratios including racemates. In the case of a E/Z isomerism, or cis/trans isomerism, for example on double bonds or rings such as cycloalkyl rings, the invention includes both the E form and Z form, or the cis form and the trans form, as well as mixtures of these forms in all ratios. In one embodiment of the invention, a compound which can occur in two or more stereoisomeric forms is a pure, or substantially pure, individual stereoisomer. The preparation of individual stereoisomers can be carried out, for example, by separation of a mixture of isomers by customary methods, for example by chromatography or crystallization, by the use of stereochemically uniform starting materials in the synthesis, or by stereoselective synthesis. Optionally, a derivatization can be carried out before a separation of stereoisomers. The separation of a mixture of stereoisomers can be carried out at the stage of the compound of the formula I or at the stage of a starting material or an intermediate during the synthesis. The present invention also includes all tautomeric forms of the compounds of the formula I and their salts and solvates.

In case the compounds of the formula I contain one or more acidic and/or basic groups, i.e. salt-forming groups, the invention also includes their corresponding physiologically or toxicologically acceptable salts, i.e. non-toxic salts, in particular their pharmaceutically acceptable salts. Thus, the compounds of the formula I which contain an acidic group, such as a hydroxycarbonyl group (=carboxy group =C(O)—OH group), can be present on such groups, and can be used according to the invention, as alkaline metal salts, alkaline earth metal salts or as ammonium salts, for example. More specific examples of such salts include sodium salts, potassium salts, calcium salts, magnesium salts, quaternary ammonium salts such as tetraalkylammonium salts, or acid addition salts with ammonia or organic amines such as, for example, ethylamine, ethanolamine, triethanolamine or amino acids. Compounds of the formula I which contain a basic group, i.e. a group which can be protonated such as an amino group or a nitrogen heterocycle, can be present on such groups, and can be used according to the invention, in the form of their addition salts with inorganic and organic acids. Examples for suitable acids include hydrogen chloride, hydrogen bromide, phosphoric acid, sulfuric acid, methanesulfonic acid, oxalic acid, acetic acid, trifluoroacetic acid, tartaric acid, lactic acid, benzoic acid, malonic acid, fumaric acid, maleic acid, citric acid, and other acids known to the person skilled in the art. If a compound of the formula I simultaneously contains an acidic group and a basic group in the molecule, the invention also includes, in addition to the salt forms mentioned, inner salts (=betaines, zwitterions). The salts of the compounds of the formula I can be obtained by customary methods which are known to the person skilled in the art like, for example, by contacting the compound of the formula I with an organic or inorganic acid or base in a solvent or diluent, or by anion exchange or cation exchange from another salt. The invention also includes all salts of the compounds of the formula I which, owing to low physiological compatibility of the salt-forming acid or base, are not directly suitable for use in pharmaceuticals but which can be used, for example, as intermediates for chemical reactions or for the preparation of physiologically acceptable salts.

The present invention furthermore includes all solvates of compounds of the formula I, for example hydrates or adducts with alcohols such as ($C_1$-$C_4$)-alkanols, active metabolites of the compounds of the formula I, and also prodrugs and derivatives of the compounds of the formula I which in vitro may not necessarily exhibit pharmacological activity but which in vivo are converted into pharmacologically active compounds, for example esters or amides of carboxylic acid groups.

In one embodiment of the invention, A is chosen from NH and O, in another embodiment, A is chosen from NH and S, in another embodiment A is chosen from O and S, in another embodiment A is NH, in another embodiment A is O, in another embodiment A is S.

The alkanediyl, alkenediyl and alkynediyl groups occurring in the group X can be linear or branched, as already indicated with respect to such groups in general, and these groups as well as cycloalkanediyl groups representing X can be bonded to the adjacent groups, i.e. to the group $R^4O$—C(O) and to the group $R^2$ or, in the case of the group alkanediyl-oxy, to the oxygen atom of the alkanediyl-oxy group via any positions. The said adjacent groups can be bonded to the same carbon atom or to different carbon atoms in the group X. In one embodiment, the chain of carbon atoms in an alkanediyl, alkenediyl and alkynediyl groups occurring in the group X which directly connects the group $R^4O$—C(O) to the group $R^2$ or, in the case of the group alkanediyl-oxy, to the oxygen atom of the alkanediyl-oxy group, consists of 1, 2, 3 or 4 carbon atoms, in another embodiment of 1, 2 or 3 carbon atoms, in another embodiment of 1 or 2 carbon atoms, in another embodiment of 1 carbon atom. In the case of a cycloalkanediyl group representing X, in one embodiment the groups $R^4O$—C(O) and $R^2$ are bonded to two ring carbon atoms which are in 1,2-position, 1,3-position or 1,4-position with respect to each other, in another embodiment in 1,2-position or 1,3-position with respect to each other, in another embodiment in 1,2-position with respect to each other, in another embodiment in 1,4-position with respect to each other. In one embodiment, X is chosen from ($C_1$-$C_6$)-alkanediyl, ($C_2$-$C_6$)-alkenediyl, ($C_3$-$C_7$)-cycloalkanediyl and ($C_1$-$C_6$)-alkanediyl-oxy, in another embodiment from ($C_1$-$C_6$)-alkanediyl, ($C_2$-$C_6$)-alkenediyl and ($C_1$-$C_6$)-alkanediyl-oxy, In another embodiment from ($C_1$-$C_6$)-alkanediyl, ($C_3$-$C_7$)-cycloalkanediyl and ($C_1$-$C_6$)-alkanediyl-oxy, in one embodiment from ($C_1$-$C_6$)-alkanediyl and ($C_1$-$C_6$)-alkanediyl-oxy, in another embodiment from ($C_1$-$C_6$)-alkanediyl, ($C_2$-$C_6$)-alkenediyl, ($C_2$-$C_6$)-alkynediyl and ($C_3$-$C_7$)-cycloalkanediyl, in another embodiment from ($C_1$-$C_6$)-alkanediyl, ($C_2$-$C_6$)-alkenediyl and ($C_3$-$C_7$)-cycloalkanediyl, in another embodiment from ($C_1$-$C_6$)-alkanediyl and ($C_2$-$C_6$)-alkenediyl, in another embodiment X is ($C_1$-$C_6$)-alkanediyl, in another embodiment X is ($C_2$-$C_6$)-alkenediyl, in another embodiment X is ($C_3$-$C_7$)-cycloalkanediyl, and in another embodiment X is ($C_1$-$C_6$)-alkanediyl-oxy, which all are optionally substituted as indicated. In one embodiment a ($C_1$-$C_6$)-alkanediyl group occurring in X is a ($C_1$-$C_4$)-alkanediyl group, in another embodiment a ($C_1$-$C_3$)-alkanediyl group, in another embodiment a ($C_1$-$C_2$)-alkanediyl group. In one embodiment, the ($C_2$-$C_6$)-alkenediyl and ($C_2$-$C_6$)-alkynediyl groups representing X are ($C_2$-$C_4$)-alkenediyl and ($C_2$-$C_4$)-alkynediyl groups, in another embodiment ($C_2$-$C_3$)-alkenediyl and ($C_2$-$C_3$)-alkynediyl groups. In one embodiment, a ($C_3$-$C_7$)-cycloalkanediyl group representing X is a ($C_3$-$C_6$)-cycloalkanediyl group, in another embodiment a ($C_3$-$C_4$)-cycloalkanediyl group, in another embodiment a cyclopropanediyl group, in another embodiment a cyclohexanediyl group. Examples of groups X from any one or more of which the respective group representing X can be chosen in the afore-mentioned embodiments, or from any one or more which X is chosen in another embodiment of the invention, are methylene, —CH($CH_3$)— (ethane-1,1-diyl), —$CH_2$—$CH_2$— (ethane-1,2-diyl, 1,2-ethylene), —C($CH_3$)$_2$— (1-methyl-ethane-1,1-diyl), —$CH_2$—$CH_2$—$CH_2$— (propane-1,3-diyl, 1,3-propylene), —$CH_2$—CH($CH_3$)— and —CH($CH_3$)—$CH_2$— (propane-1,2-diyl, 1,2-propylene), which exemplify the group ($C_1$-$C_6$)-alkanediyl, —CH=CH— (ethene-1,2-diyl), —CH=CH—$CH_2$— and —$CH_2$—CH=CH— (prop-1-ene-1,3-diyl and prop-2-ene-1,3-diyl) and —CH=C($CH_3$)— and —C($CH_3$)=CH— (prop-1-ene-1,2-diyl) which exemplify the group ($C_2$-$C_6$)-alkenediyl, —C≡C— (ethynediyl) and —$CH_2$—C≡C— and —C≡C—$CH_2$— (prop-1-yne-1,3-diyl and prop-2-yne-1,3-diyl) which exemplify the group ($C_2$-$C_6$)-alkynediyl, cyclopropane-1,1-diyl, cyclopropane-1,2-diyl and cyclohexane-1,4-diyl which exemplify the group ($C_3$-$C_7$)-cycloalkanediyl, —$CH_2$—O-(methylene-oxy), —$CH_2$—$CH_2$—O— (ethane-1,2-diyl-oxy), —CH($CH_3$)—O— (ethane-1,1-diyl-oxy), —C($CH_3$)$_2$—O— (1-methyl-ethane-1,1-diyl-oxy), —$CH_2$—$CH_2$—$CH_2$—O— (propane-1,3-diyl-oxy) and —$CH_2$—$CH_2$—$CH_2$—$CH_2$—O— (butane-1,4-diyl-oxy) which exemplify the group ($C_1$-$C_6$)-alkanediyl-oxy, all of which are optionally substituted as indicated. Thus, in one embodiment X is chosen from —$CH_2$—O—, —$CH_2$—$CH_2$—O—, —CH($CH_3$)—O— and —C($CH_3$)$_2$—O—, in another embodiment from —$CH_2$—O—, —$CH_2$—$CH_2$—O— and —CH($CH_3$)—O—, in another embodiment from —$CH_2$—O— and —CH($CH_3$)—O—, and in another embodiment X is —$CH_2$—O—, all of which are optionally substituted as indicated, and in which the oxygen atom is bonded to the group $R^2$. In one embodiment, the number of substituents which are optionally present in X, is 1, 2, 3 or 4, in another embodiment 1, 2 or 3, in another embodiment 1 or 2, in another embodiment 1, and in another embodiment the group X is not substituted by substituents chosen from fluorine and hydroxy. In one embodiment, the number of hydroxy substituents in X is not greater than 2, in another embodiment not greater than 1. In one embodiment, no more than one hydroxy substituent is present on an individual carbon atom in X. In one embodiment, hydroxy substituents are not present on carbon atoms which are part of a double bond in the group ($C_2$-$C_6$)-alkenediyl. In one embodiment, hydroxy substituents are not present on the carbon atom in the group ($C_1$-$C_6$)-alkanediyl-oxy which is bonded to the oxygen atom, in another embodiment no substituents are present on the carbon atom in the group ($C_1$-$C_6$)-alkanediyl-oxy which is bonded to the oxygen atom, i.e. in this latter embodiment all carbon atoms which are not linked to the said oxygen atom are optionally substituted by one or more identical or different substituents chosen from fluoro and hydroxy. The double bond in the group ($C_2$-$C_6$)-alkenediyl can have E configuration or Z configuration. In one embodiment it has E configuration, in another embodiment it has Z configuration.

In one embodiment of the invention, the number z is chosen from 0 and 1, in another embodiment it is 0, in another embodiment it is 1. In one embodiment of the invention, the group $R^1$ is chosen from hydrogen and ($C_1$-$C_4$)-alkyl, in another embodiment $R^1$ is chosen from hydrogen, methyl, ethyl, n-propyl, n-butyl and isopropyl, in another embodiment from hydrogen, methyl and ethyl, in another embodiment $R^1$ is hydrogen, in another embodiment $R^1$ is $(C_1$-$C_4)$-alkyl, in another embodiment $R^1$ is methyl, and in another embodiment $R^4$ is ethyl. In one embodiment, a $(C_3$-$C_7)$-cycloalkyl group occurring in $R^1$ is $(C_3$-$C_6)$-cycloalkyl, in another embodiment it is cyclopropyl.

In one embodiment of the invention, the number of ring heteroatoms in an aromatic heterocycle representing $R^2$ is 1 or 2, in another embodiment it is 1. In one embodiment of the invention, $R^2$ is chosen from phenylene and a divalent residue of an aromatic, 6-membered monocyclic heterocycle which comprises 1, 2 or 3 ring nitrogen atoms, in another embodiment 1 or 2 ring nitrogen atoms, in another embodiment 1 ring nitrogen atom, wherein one of the ring nitrogen atoms can carry a substituent $R^{21}$ which is oxy, i.e. wherein one of the ring nitrogen atoms can be oxidized to the N-oxide, and wherein the phenylene and divalent residue of an aromatic heterocycle are optionally substituted on one or more ring carbon atoms by identical or different substituents $R^{22}$. In another embodiment, $R^2$ is phenylene, wherein the phenylene is optionally substituted on one or more ring atoms by identical or different substituents $R^{22}$, and in another embodiment $R^2$ is pyridinediyl, wherein the ring nitrogen atom can carry a substituent $R^{21}$ which is oxy, i.e. wherein the ring nitrogen atom can be oxidized to the N-oxide, and wherein the pyridinediyl is optionally substituted on one or more ring carbon atoms by identical or different substituents $R^{22}$. In another embodiment, $R^2$ is a divalent residue of an aromatic 5-membered heterocycle which comprises 1, 2 or 3 identical or different ring heteroatoms chosen from N, O and S, wherein one of the ring nitrogen atoms can carry a hydrogen atom or a substituent $R^{21}$, and wherein the divalent residue of an aromatic heterocycle is optionally substituted on one or more ring carbon atoms by identical or different substituents $R^{22}$. In one embodiment, a divalent residue of an aromatic heterocyclic group representing $R^2$ is chosen from furandiyl, thiophenediyl, oxazolediyl, thiazolediyl, pyridinediyl, pyridazinediyl, pyrimidinediyl and pyrazinediyl, in another embodiment from furandiyl, thiophenediyl, thiazolediyl, pyridinediyl, pyridazinediyl, pyrimidinediyl and pyrazinediyl, in another embodiment from furandiyl, thiophenediyl, pyridinediyl, pyridazinediyl, pyrimidinediyl and pyrazinediyl, in another embodiment from furandiyl, thiophenediyl, pyridinediyl and pyrimidinediyl, in another embodiment from furandiyl, thiophenediyl and pyridinediyl, which are all optionally substituted as indicated with respect to $R^2$.

The ring carbon atoms via which the phenylene group and the divalent residue of an aromatic heterocycle representing $R^2$ are bonded to the oxazolopyrimidine ring and to the group X, can be in any positions. A phenylene group representing $R^2$ can be 1,2-phenylene, i.e. the oxazolopyrimidine ring and the group X can be bonded in 1,2-position, or ortho position, with respect to each another, it can be 1,3-phenylene, i.e. the oxazolopyrimidine ring and the group X can be bonded in 1,3-position, or meta position, with respect to each another, and it can be 1,4-phenylene, i.e. the oxazolopyrimidine ring and the group X can be bonded in 1,4-position, or para position, with respect to each another. In one embodiment, a phenylene group representing $R^2$ is chosen from 1,3-phenylene and 1,4-phenylene, in another embodiment it is 1,3-phenylene, and in another embodiment it is 1,4-phenylene, which all are optionally substituted as indicated with respect to $R^2$. In one embodiment, $R^2$ is chosen from one or more of the groups phenylene, furan-2,5-diyl, thiophene-2,4-diyl, thiophene-2,5-diyl, pyridine-2,4-diyl, pyridine-2,5-diyl, pyridine-3,5-diyl, pyridine-2,6-diyl and pyrimidine-2,5-diyl, in another embodiment from the groups furan-2,5-diyl, thiophene-2,4-diyl, thiophene-2,5-diyl, pyridine-2,4-diyl, pyridine-2,5-diyl, pyridine-3,5-diyl, pyridine-2,6-diyl and pyrimidine-2,5-diyl, in another embodiment from pyridine-2,4-diyl, pyridine-2,5-diyl, pyridine-3,5-diyl and pyridine-2,6-diyl, in another embodiment from phenylene, pyridine-2,4-diyl, pyridine-2,5-diyl, pyridine-3,5-diyl and pyridine-2,6-diyl, which all are optionally substituted as indicated with respect to $R^2$. In one embodiment, the number of substituents $R^{22}$ which are optionally present on ring carbon atoms in $R^2$, is 1, 2, 3, 4 or 5, in another embodiment 1, 2, 3 or 4, in another embodiment 1, 2 or 3, in another embodiment 1 or 2, in another embodiment 1. Ring carbon atoms in $R^2$ which do not carry a substituent $R^{22}$, carry a hydrogen atom.

In one embodiment of the invention, $R^3$ is chosen from $(C_1$-$C_6)$-alkyl, $(C_2$-$C_6)$-alkenyl and $(C_2$-$C_6)$-alkynyl, in another embodiment $R^3$ is $(C_1$-$C_6)$-alkyl, in another embodiment $R^3$ is $(C_2$-$C_5)$-alkyl, and in another embodiment $R^3$ is $(C_1$-$C_4)$-alkyl. In another embodiment $R^3$ is chosen from $(C_1$-$C_6)$-alkyl, $(C_3$-$C_7)$-cycloalkyl-$C_uH_{2u}$— and Het-$C_vH_{2v}$—, in another embodiment from $(C_3$-$C_7)$-cycloalkyl-$C_uH_{2u}$— and Het-$C_vH_{2v}$—, in another embodiment $R^3$ is $(C_3$-$C_7)$-cycloalkyl-$C_uH_{2u}$—, and in another embodiment $R^3$ is Het-$C_vH_{2v}$—, wherein in these embodiment u and v independently of each other are chosen from 1 and 2. In one embodiment u is 1, in another embodiment u is 2. In one embodiment v is 1, in another embodiment v is 2. In one embodiment, the group $(C_3$-$C_7)$-cycloalkyl-$C_uH_{2u}$— representing $R^3$ is chosen from cyclopropyl-$C_uH_{2u}$—, cyclobutyl-$C_uH_{2u}$— and cyclopentyl-$C_uH_{2u}$— and the group Het-$C_vH_{2v}$-representing $R^3$ is tetrahydrofuranyl-$C_vH_2$—. In one embodiment, $R^3$ is chosen from cyclopropyl-$C_uH_{2u}$—, cyclobutyl-$C_uH_{2u}$— and cyclopentyl-$C_uH_{2u}$—.

In one embodiment, $R^3$ is chosen from $(C_3$-$C_7)$-cycloalkyl-$C_uH_{2u}$— and Het-$C_vH_{2v}$—, or $R^3$ is a residue of a saturated or unsaturated, 3-membered to 10-membered, monocyclic or bicyclic ring which comprises 0, 1, 2, 3 or 4 identical or different ring heteroatoms chosen from N, O and S, wherein one or two of the ring nitrogen atoms can carry a hydrogen atom or a $(C_1$-$C_4)$-alkyl substituent and one or two of the ring sulfur atoms can carry one or two oxo groups, and wherein the residue of a ring is optionally substituted on one or more ring carbon atoms by identical or different substituents $R^{31}$, and in another embodiment $R^3$ is a residue of a saturated or unsaturated, 3-membered to 10-membered, monocyclic or bicyclic ring which comprises 0, 1, 2, 3 or 4 identical or different ring heteroatoms chosen from N, O and S, wherein one or two of the ring nitrogen atoms can carry a hydrogen atom or a $(C_1$-$C_4)$-alkyl substituent and one or two of the ring sulfur atoms can carry one or two oxo groups, and wherein the residue of a ring is optionally substituted on one or more ring carbon atoms by identical or different substituents $R^{31}$. In one embodiment, the number of ring heteroatoms in the ring representing $R^3$ is 0, 1, 2 or 3, in another embodiment it is 0, 1 or 2, in another embodiment it is 0 or 1, in another embodiment it is 0, in another embodiment it is 1, 2, 3 or 4, in another embodiment it is 1, 2 or 3, in another embodiment it is 1 or 2, in another embodiment it is 1. The residue of the ring representing $R^3$ can thus be carbocyclic or heterocyclic. In one embodiment, the ring heteroatoms in $R^3$ are chosen from N and O, in another embodiment from N and S, in another embodiment from O and S, in another embodiment they are N, wherein ring nitrogen atoms can carry a hydrogen atom or a $(C_1$-$C_4)$-alkyl substituent as occurs in saturated or partially unsaturated heterocycles or in 5-membered aromatic rings in heterocycles such as pyrrole or benzoimidazole, for example, or not carry a hydrogen atom or a ($C_1$-$C_4$)-alkyl substituent as occurs in aromatic heterocycles such as imidazole or pyridine, for example. In a residue of a heterocycle representing $R^3$ which comprises one or more ring sulfur atoms, in one embodiment one of the ring sulfur atoms is non-oxidized or carries one or two oxo groups, and any other ring sulfur atoms are non-oxidized. The residue of a monocyclic or bicyclic ring representing $R^3$ can be bonded to the group A via any suitable ring carbon atom or ring nitrogen atom. In one embodiment it is bonded via a ring carbon atom, in another embodiment it is bonded via a ring carbon atom or, in case A is NH, via a ring nitrogen atom, and in another embodiment it is bonded via a ring a ring nitrogen atom. The residue of a monocyclic or bicyclic ring representing $R^3$ can be unsaturated and in this case contain 1, 2, 3, 4 or 5, or 1, 2, 3 or 4, or 1, 2 or 3, or 1 or 2, or 1, double bonds within the ring and can in any of the one or two rings be aromatic or non-aromatic, or it can be saturated and in this latter case contain no double bonds within the ring. In one embodiment, the residue of the ring representing $R^3$ is saturated or aromatic, in another embodiment it is saturated, and in another embodiment it is aromatic. In one embodiment, the residue of 3-membered or 4-membered ring representing $R^3$ is saturated. If $R^3$ comprises ring nitrogen atoms which can carry a hydrogen atom or a ($C_1$-$C_4$)-alkyl substituent, one of such ring nitrogen atoms or two of such ring nitrogen atoms can be present. In one embodiment, the number of optional substituents $R^{31}$ on ring carbon atoms in the ring representing $R^3$ is 1, 2, 3, 4, 5 or 6, in another embodiment 1, 2, 3, 4 or 5, in another embodiment 1, 2, 3 or 4, in another embodiment 1, 2 or 3, in another embodiment 1 or 2, in another embodiment 1.

The ring which can represent $R^3$ can be 3-membered, 4-membered, 5-membered, 6-membered, 7-membered, 8-membered, 9-membered or 10 membered. In one embodiment, $R^3$ is 4-membered to 10-membered, in another embodiment 4-membered to 9-membered, in another embodiment 4-membered to 8-membered, in another embodiment 4-membered to 7-membered, in another 5-membered to 7-membered, in another embodiment 5-membered or 6-membered, in another embodiment 6-membered, in another embodiment 8-membered to 10-membered, in another embodiment 9-membered to 10-membered. In one embodiment, a 3-membered ring representing $R^3$ does not comprise any ring heteroatoms. In one embodiment, $R^3$ is monocyclic, in another embodiment bicyclic. In one embodiment, a bicyclic group representing $R^3$ is at least 7-membered. Among others, the residue of a ring representing $R^3$ can be a cycloalkyl group, a phenyl group, a naphthyl group, a residue of an unsaturated, aromatic or non-aromatic heterocyclic group or a residue of a saturated heterocyclic group, which all are optionally substituted on ring carbon atoms and ring nitrogen atoms as specified with respect to $R^3$. As far as applicable, all explanations given above with respect to such groups apply correspondingly to $R^3$. Another example of groups which can represent $R^3$, are cycloalkenyl groups such as ($C_5$-$C_7$)-cycloalkenyl groups which can be bonded via any ring carbon atom and are optionally substituted as specified with respect to $R^3$. In one embodiment, optional substituents $R^{31}$ on a cycloalkenyl group representing $R^3$ are chosen from fluorine and ($C_1$-$C_4$)-alkyl. In one embodiment, cycloalkenyl groups contain one double bond within the ring which can be present in any position. Examples of cycloalkenyl are cyclopentenyl including cyclopent-1-enyl, cyclopent-2-enyl and cyclopent-3-enyl, cyclohexenyl including cyclohex-1-enyl, cyclohex-2-enyl and cyclohex-3-enyl, and cycloheptenyl including cyclohept-1-enyl, cyclohept-2-enyl, cyclopent-3-enyl and cyclohept-4-enyl. Examples of residues of rings, from any one or more of which $R^3$ is chosen in one embodiment of the invention, are cyclopropyl, cyclobutyl, cyclopentyl, cyclohexyl, phenyl, oxetanyl including oxetan-3-yl, tetrahydrofuranyl including tetrahydrofuran-3-yl, tetrahydrothiophenyl including tetrahydrothiophen-3-yl, tetrahydropyranyl including tetrahydropyran-4-yl, azetidinyl including azetidin-1-yl, pyrrolidinyl, piperidinyl, imidazolidinyl, piperazin-yl, morpholinyl including morpholin-1-yl, thiomorpholinyl, furanyl including furan-3-yl, thiophenyl including thiophen-3-yl, pyrazolyl including pyrazol-3-yl, imidazolyl, thiazolyl including thiazol-2-yl, pyridinyl including pyridin-2-yl, pyridin-3-yl and pyridin-4-yl, pyridazinyl including pyridazin-3-yl, wherein in all of them, if applicable, one or two of the ring nitrogen atoms can carry a hydrogen atom or ($C_1$-$C_4$)-alkyl, and wherein all of them are optionally substituted on one or more ring carbon atoms by identical or different substituents $R^{31}$, and wherein in all of them, if applicable, a ring sulfur atom can be non-oxidized, i.e. be present as a sulfur atom, or carry one or two oxo groups, i.e. be present in the form of a sulfoxide or sulfone.

In one embodiment, $R^3$ is chosen from phenyl and a residue of a saturated or unsaturated 3-membered to 7-membered, monocyclic ring, in another embodiment from phenyl and a residue of a saturated or unsaturated 5-membered to 7-membered, monocyclic ring, in another embodiment from phenyl, pyridinyl and a residue of a saturated 3-membered to 7-membered, monocyclic ring, in another embodiment from phenyl, pyridinyl and a residue of a saturated 5-membered to 7-membered, monocyclic ring, in another embodiment from phenyl and pyridinyl, in another embodiment from phenyl and a residue of a saturated 3-membered to 7-membered, monocyclic ring, in another embodiment from phenyl and a residue of a saturated 5-membered to 7-membered, monocyclic ring, wherein in all these embodiments the monocyclic ring comprises 1 or 2 identical or different ring heteroatoms chosen from N, O and S, wherein one or two of the ring nitrogen atoms can carry a hydrogen atom or a ($C_1$-$C_4$)-alkyl substituent and one or two of the ring sulfur atoms can carry one or two oxo groups, and wherein the phenyl, pyridinyl and residue of a ring are optionally substituted on one or more ring carbon atoms by identical or different substituents $R^{31}$, and wherein pyridinyl includes pyridin-2-yl, pyridin-3-yl and pyridin-4-yl. In another embodiment, $R^3$ is phenyl which is optionally substituted by one or more identical or different substituents $R^{31}$.

In one embodiment of the invention, the number w is chosen from 0 and 1, in another embodiment it is 0, in another embodiment it is 1. In one embodiment, a ($C_3$-$C_7$)-cycloalkyl group present in $R^{21}$ is ($C_3$-$C_6$)-cycloalkyl, in another embodiment ($C_3$-$C_5$)-cycloalkyl, in another embodiment cyclopropyl. In one embodiment, $R^{21}$ is chosen from ($C_1$-$C_4$)-alkyl and oxy, in another embodiment $R^{21}$ is ($C_1$-$C_4$)-alkyl, in another embodiment it is ($C_1$-$C_3$)-alkyl, in another embodiment it is methyl, and in another embodiment it is oxy.

In one embodiment of the invention, the substituents $R^{22}$ which are optionally present on the group $R^2$, are chosen from halogen, hydroxy, ($C_1$-$C_4$)-alkyl-, ($C_1$-$C_4$)-alkyloxy-, ($C_1$-$C_4$)-alkyl-$S(O)_m$—, amino, nitro and cyano, in another embodiment from halogen, hydroxy, ($C_1$-$C_4$)-alkyl-, ($C_1$-$C_4$)-alkyloxy-, amino and cyano-, in another embodiment from halogen, hydroxy, ($C_1$-$C_4$)-alkyl- and ($C_1$-$C_4$)-alkyloxy-, in another embodiment from fluorine, chlorine, hydroxy, ($C_1$-$C_4$)-alkyl- and ($C_1$-$C_4$)-alkyloxy-, in another embodiment from fluorine, chlorine and ($C_1$-$C_4$)-alkyl-, and in another embodiment they are ($C_1$-$C_4$)-alkyl substituents.

In one embodiment, 1, 2 or 3 of the substituents $R^{22}$, in another embodiment 1 or 2 of the substituents $R^{22}$, and in another embodiment 1 of the substituents $R^{22}$, which are optionally present on the group $R^2$, are defined as in the general definition of $R^{22}$ and thus are chosen from halogen, hydroxy, $(C_1-C_4)$-alkyl-, $(C_1-C_4)$-alkyloxy-, $(C_1-C_4)$-alkyl-S$(O)_m$—, amino, nitro, cyano, hydroxycarbonyl, $(C_1-C_4)$-alkyloxycarbonyl, aminocarbonyl and aminosulfonyl-, and any further substituents $R^{22}$ which are optionally present on the group $R^2$, for example 1, 2 or 3 further substituents $R^{22}$, or 1 or 2 further substituents $R^{22}$, or 1 further substituent $R^{22}$, are chosen from halogen, hydroxy, $(C_1-C_4)$-alkyl-, $(C_1-C_4)$-alkyloxy-, $(C_1-C_4)$-alkyl-S$(O)_m$—, amino, nitro and cyano, wherein all alkyl groups independently of each other are optionally substituted by one or more fluorine substituents as generally applies to alkyl groups. In one embodiment, the said substituents $R^{22}$ which are optionally present on the group $R^2$ and which in the afore-mentioned embodiment are defined as in the general definition of $R^{22}$, for example 1 or 2 such substituents $R^{22}$, or 1 such substituent $R^{22}$, are chosen from halogen, hydroxy, $(C_1-C_4)$-alkyl-, $(C_1-C_4)$-alkyloxy-, $(C_1-C_4)$-alkyl-S$(O)_m$—, amino and cyano. In one embodiment, the said substituents $R^{22}$ which are optionally present on the group $R^2$ and which in the afore-mentioned embodiment are defined as in the general definition of $R^{22}$, for example 1 or 2 such substituents $R^{22}$, or 1 such substituent $R^{22}$, are not located on ring carbon atoms within the group $R^2$ which are adjacent to the atom via which the group $R^2$ is bonded to the oxazolopyrimidine ring depicted in formula I. In one embodiment, the said further substituents $R^{22}$ which are optionally present on the group $R^2$, for example 1, 2 or 3 further substituents $R^{22}$, or 1 or 2 further substituents $R^{22}$, or 1 further substituent $R^{22}$, are chosen from halogen, hydroxy, $(C_1-C_4)$-alkyl-, $(C_1-C_4)$-alkyloxy-, amino, cyano, in another embodiment from halogen, hydroxy, $(C_1-C_4)$-alkyl- and $(C_1-C_4)$-alkyloxy-, in another embodiment from halogen, $(C_1-C_4)$-alkyl- and $(C_1-C_4)$-alkyloxy-, in another embodiment from halogen and $(C_1-C_4)$-alkyl-, wherein in all these embodiments all alkyl groups independently of each other are optionally substituted by one or more fluorine substituents.

In one embodiment of the invention, $R^{31}$ is chosen from halogen, $(C_1-C_4)$-alkyl, $(C_3-C_7)$-cycloalkyl, hydroxy, $(C_1-C_4)$-alkyloxy, oxo, $(C_1-C_4)$-alkyl-S$(O)_m$—, amino, $(C_1-C_4)$-alkylamino, di$((C_1-C_4)$-alkyl)amino, $(C_1-C_4)$-alkylcarbonylamino, $(C_1-C_4)$-alkylsulfonylamino, cyano, $(C_1-C_4)$-alkylcarbonyl, aminosulfonyl, $(C_1-C_4)$-alkylaminosulfonyl and di$((C_1-C_4)$-alkyl)aminosulfonyl, in another embodiment from halogen, $(C_1-C_4)$-alkyl, $(C_3-C_7)$-cycloalkyl, hydroxy, $(C_1-C_4)$-alkyloxy, oxo, $(C_1-C_4)$-alkyl-S$(O)_m$—, amino, $(C_1-C_4)$-alkylamino, di$((C_1-C_4)$-alkyl)amino, cyano, aminosulfonyl, $(C_1-C_4)$-alkylaminosulfonyl and di$((C_1-C_4)$-alkyl)aminosulfonyl, in another embodiment from halogen, $(C_1-C_4)$-alkyl, $(C_3-C_7)$-cycloalkyl, hydroxy, $(C_1-C_4)$-alkyloxy, oxo, $(C_1-C_4)$-alkyl-S$(O)_m$—, amino, $(C_1-C_4)$-alkylamino, di$((C_1-C_4)$-alkyl)amino, cyano and aminosulfonyl, in another embodiment from halogen, $(C_1-C_4)$-alkyl, $(C_3-C_7)$-cycloalkyl, hydroxy, $(C_1-C_4)$-alkyloxy, oxo, amino, $(C_1-C_4)$-alkylamino, di$((C_1-C_4)$-alkyl)amino, cyano and aminosulfonyl, in another embodiment from halogen, $(C_1-C_4)$-alkyl, $(C_3-C_7)$-cycloalkyl, hydroxy, $(C_1-C_4)$-alkyloxy, oxo, amino, $(C_1-C_4)$-alkylamino and di$((C_1-C_4)$-alkyl)amino, in another embodiment from halogen, $(C_1-C_4)$-alkyl, $(C_3-C_7)$-cycloalkyl, $(C_1-C_4)$-alkyloxy and di$((C_1-C_4)$-alkyl)amino, in another embodiment from halogen, $(C_1-C_4)$-alkyl, $(C_3-C_7)$-cycloalkyl, hydroxy and $(C_1-C_4)$-alkyloxy, in another embodiment from halogen, $(C_1-C_4)$-alkyl and $(C_1-C_4)$-alkyloxy, in another embodiment from fluorine, chlorine, $(C_1-C_4)$-alkyl, $(C_3-C_7)$-cycloalkyl, hydroxy and $(C_1-C_4)$-alkyloxy, wherein in all these embodiments all alkyl groups independently of each other are optionally substituted by one or more fluorine substituents.

In one embodiment, the optional substituents $R^{31}$ on the residue of an aromatic ring representing $R^3$, for example on a phenyl group or pyridinyl group representing $R^3$, are chosen from halogen, $(C_1-C_4)$-alkyl, $(C_3-C_7)$-cycloalkyl, hydroxy, $(C_1-C_4)$-alkyloxy, $(C_1-C_4)$-alkyl-S$(O)_m$—, amino, $(C_1-C_4)$-alkylamino, di$((C_1-C_4)$-alkyl)amino, $(C_1-C_4)$-alkylcarbonylamino, $(C_1-C_4)$-alkylsulfonylamino, cyano, $(C_1-C_4)$-alkylcarbonyl, aminosulfonyl, $(C_1-C_4)$-alkylaminosulfonyl and di$((C_1-C_4)$-alkyl)aminosulfonyl, in another embodiment from halogen, $(C_1-C_4)$-alkyl, $(C_3-C_7)$-cycloalkyl, hydroxy, $(C_1-C_4)$-alkyloxy, $(C_1-C_4)$-alkyl-S$(O)_m$—, amino, $(C_1-C_4)$-alkylamino, di$((C_1-C_4)$-alkyl)amino, cyano, aminosulfonyl, $(C_1-C_4)$-alkylaminosulfonyl and di$((C_1-C_4)$-alkyl)aminosulfonyl, in another embodiment from halogen, $(C_1-C_4)$-alkyl, $(C_3-C_7)$-cycloalkyl, hydroxy, $(C_1-C_4)$-alkyloxy, $(C_1-C_4)$-alkyl-S$(O)_m$—, amino, $(C_1-C_4)$-alkylamino, di$((C_1-C_4)$-alkyl)amino, cyano and aminosulfonyl, in another embodiment from halogen, $(C_1-C_4)$-alkyl, $(C_3-C_7)$-cycloalkyl, hydroxy, $(C_1-C_4)$-alkyloxy, amino, $(C_1-C_4)$-alkylamino, di$((C_1-C_4)$-alkyl)amino, cyano and aminosulfonyl, in another embodiment from halogen, $(C_1-C_4)$-alkyl, $(C_3-C_7)$-cycloalkyl, hydroxy, $(C_1-C_4)$-alkyloxy, amino, $(C_1-C_4)$-alkylamino and di$((C_1-C_4)$-alkyl)amino, in another embodiment from halogen, $(C_1-C_4)$-alkyl, $(C_3-C_7)$-cycloalkyl, $(C_1-C_4)$-alkyloxy and di$((C_1-C_4)$-alkyl)amino, in another embodiment from halogen, $(C_1-C_4)$-alkyl, $(C_3-C_7)$-cycloalkyl, hydroxy and $(C_1-C_4)$-alkyloxy, in another embodiment from halogen, $(C_1-C_4)$-alkyl and $(C_1-C_4)$-alkyloxy, in another embodiment from fluorine, chlorine, $(C_1-C_4)$-alkyl, $(C_3-C_7)$-cycloalkyl, hydroxy and $(C_1-C_4)$-alkyloxy, wherein in all these embodiments all alkyl groups independently of each other are optionally substituted by one or more fluorine substituents.

In one embodiment, the optional substituents $R^{31}$ on the residue of a saturated or non-aromatic unsaturated ring representing $R^3$ are chosen from halogen, $(C_1-C_4)$-alkyl, $(C_3-C_7)$-cycloalkyl, hydroxy, $(C_1-C_4)$-alkyloxy, oxo, $(C_1-C_4)$-alkyl-S$(O)_m$—, amino, $(C_1-C_4)$-alkylamino, di$((C_1-C_4)$-alkyl)amino, $(C_1-C_4)$-alkylcarbonylamino, $(C_1-C_4)$-alkylsulfonylamino and cyano, in another embodiment from halogen, $(C_1-C_4)$-alkyl, $(C_3-C_7)$-cycloalkyl, hydroxy, $(C_1-C_4)$-alkyloxy, oxo, amino, $(C_1-C_4)$-alkylamino, di$((C_1-C_4)$-alkyl)amino and cyano, in another embodiment from halogen, $(C_1-C_4)$-alkyl, $(C_3-C_7)$-cycloalkyl, hydroxy, $(C_1-C_4)$-alkyloxy and oxo, in another embodiment from halogen, $(C_1-C_4)$-alkyl, hydroxy, $(C_1-C_4)$-alkyloxy and oxo, in another embodiment from fluorine, chlorine, $(C_1-C_4)$-alkyl, hydroxy, $(C_1-C_4)$-alkyloxy and oxo, in another embodiment from $(C_1-C_4)$-alkyl, hydroxy and oxo, in another embodiment from alkyl and hydroxy, and in another embodiment they are $(C_1-C_4)$-alkyl, wherein in all these embodiments all alkyl groups independently of each other are optionally substituted by one or more fluorine substituents. In case the residue of a ring representing $R^3$ contains any oxo groups as substituents $R^{31}$, in one embodiment not more than two such oxo substituents are present, and in another embodiment not more than one such oxo substituent is present.

In one embodiment of the invention, the ring heteroatoms in Het are chosen from N and O, in another embodiment from O and S, in another embodiment they are O atoms. In one embodiment, the number of ring heteroatoms in Het is 1. In one embodiment, two ring oxygen atoms in Het are not present in adjacent ring positions, in another embodiment two ring heteroatoms chosen from O and S are not present in adjacent ring positions, in another embodiment two ring heteroatoms are not present in adjacent ring positions. Ring nitrogen atoms in Het carry a hydrogen atom or a substituent as specified. In one embodiment, optional substituents on ring nitrogen atoms in Het are $(C_1-C_4)$-alkyl substituents. In one embodiment, optional substituents on ring nitrogen atoms and ring carbon atoms in Het are $(C_1-C_4)$-alkyl substituents In one embodiment, the number of optional substituents on Het is 1, 2, 3, 4 or 5, in another embodiment 1, 2, 3 or 4, in another embodiment 1, 2 or 3, in another embodiment 1 or 2, in another embodiment 1. Het can be bonded via any suitable ring carbon atom. In one embodiment, Het is bonded via a ring carbon atom which is not adjacent to a ring heteroatom. Het can be 4-membered, 5-membered, 6-membered or 7-membered. In one embodiment, Het is 4-membered or 5-membered, in another embodiment 5-membered to 7-membered, in another embodiment 5-membered or 6-membered, in another embodiment 4-membered. Examples of Het, from any one or more of which Het is chosen in one embodiment, are oxetanyl including oxetan-2-yl and oxetan-3-yl, tetrahydrofuranyl including tetrahydrofuran-2-yl and tetrahydrofuran-3-yl, tetrahydropyranyl including tetrahydropyran-2-yl, tetrahydropyran-3-yl and tetrahydropyran-4-yl, oxepanyl including oxepan-2-yl, oxepan-3-yl and oxepan-4-yl, [1,3]dioxolanyl including [1,3]dioxolan-2-yl and [1,3]dioxolan-4-yl, [1,4]dioxanyl including [1,4]dioxan-2-yl, thietanyl including thietan-2-yl and thietan-3-yl, tetrahydrothiophenyl including tetrahydrothiophen-2-yl and tetrahydrothiophen-3-yl, tetrahydrothiopyranyl including tetrahydrothiopyran-2-yl, tetrahydrothiopyran-3-yl and tetrahydrothiopyran-4-yl, [1,4]dithianyl including [1,4]dithian-2-yl, azetidinyl including azetidin-2-yl and azetidin-3-yl, pyrrolidinyl including pyrrolidinyl-2-yl and pyrrolidinyl-3-yl, piperidinyl including piperidinyl-2-yl, piperidinyl-3-yl and piperidinyl-4-yl, azepanyl including azepan-2-yl, azepan-3-yl and azepan-4-yl, oxazolidinyl including oxazolidin-2-yl, oxazolidin-4-yl and oxazolidin-5-yl, thiazolidinyl including thiazolidin-2-yl, thiazolidin-4-yl and thiazolidin-5-yl, morpholinyl including morpholin-2-yl and morpholin-3-yl, thiomorpholinyl including thiomorpholin-2-yl and thiomorpholin-3-yl, which all are optionally substituted as specified with respect to Het.

A subject of the invention are all compounds of the formula I wherein any one or more structural elements such as groups, substituents and numbers are defined as in any of the specified embodiments or definitions of the elements or have any one or more of the specific meanings which are mentioned herein as examples of elements, wherein all combinations of one or more specified embodiments and/or definitions and/or specific meanings of the elements are a subject of the present invention. Also with respect to all such compounds of the formula I, all their stereoisomeric forms and mixtures of stereoisomeric forms in any ratio, and their physiologically acceptable salts, and the physiologically acceptable solvates of any of them, are a subject of the present invention.

An example of compounds of the invention which with respect to any structural elements are defined as in specified embodiments of the invention or definitions of such elements, and which are a subject of the invention, are compounds of the formula I, in any of their stereoisomeric forms, or a mixture of stereoisomeric forms in any ratio, and the physiologically acceptable salts thereof, and the physiologically acceptable solvates of any of them, wherein $R^3$ is chosen from $(C_1-C_6)$-alkyl, $(C_3-C_7)$-cycloalkyl-$C_uH_{2u}$— and Het-$C_vH_{2v}$—, wherein u and v are chosen from 1 and 2, or $R^3$ is a residue of a saturated or unsaturated, 3-membered to 10-membered, monocyclic or bicyclic ring which comprises 0, 1 or 2 identical or different ring heteroatoms chosen from N, O and S, wherein one or two of the ring nitrogen atoms can carry a hydrogen atom or a $(C_1-C_4)$-alkyl substituent and one of the ring sulfur atoms can carry one or two oxo groups, and wherein the residue of a ring is optionally substituted on one or more ring carbon atoms by identical or different substituents $R^{31}$;

Het is a residue of a saturated, 4-membered to 6-membered, monocyclic heterocycle which comprises 1 ring heteroatom chosen from N, O and S and which is bonded via a ring carbon atom, wherein the residue of a heterocycle is optionally substituted by one or more identical or different substituents chosen from fluorine and $(C_1-C_4)$-alkyl; and all other groups and numbers are defined as in the general definition of the compounds of the formula I or in any specified embodiments of the invention or definitions of structural elements.

Another such example are compounds of the formula I, in any of their stereoisomeric forms, or a mixture of stereoisomeric forms in any ratio, and the physiologically acceptable salts thereof, and the physiologically acceptable solvates of any of them, wherein A is chosen from O and S;

X is chosen from $(C_1-C_6)$-alkanediyl, $(C_2-C_6)$-alkanediyl and $(C_1-C_6)$-alkanediyl-oxy;

$R^2$ is chosen from phenylene and pyridinediyl, wherein the phenylene and the pyridinediyl are optionally substituted on one or more ring carbon atoms by identical or different substituents $R^{22}$;

$R^3$ is chosen from $(C_1-C_6)$-alkyl, $(C_3-C_7)$-cycloalkyl-$C_uH_{2u}$— and Het-$C_vH_{2v}$—, wherein u and v are chosen from 1 and 2, or $R^3$ is a residue of a saturated or unsaturated, 3-membered to 10-membered, monocyclic or bicyclic ring which comprises 0, 1 or 2 identical or different ring heteroatoms chosen from N, O and S, wherein one or two of the ring nitrogen atoms can carry a hydrogen atom or a $(C_1-C_4)$-alkyl substituent and one of the ring sulfur atoms can carry one or two oxo groups, and wherein the residue of a ring is optionally substituted on one or more ring carbon atoms by identical or different substituents $R^{31}$;

Het is a residue of a saturated, 4-membered to 6-membered, monocyclic heterocycle which comprises 1 ring heteroatom chosen from N, O and S and which is bonded via a ring carbon atom, wherein the residue of a heterocycle is optionally substituted by one or more identical or different substituents chosen from fluorine and $(C_1-C_4)$-alkyl; and all other groups and numbers are defined as in the general definition of the compounds of the formula I or in any specified embodiments of the invention or definitions of structural elements.

Another such example are compounds of the formula I, in any of their stereoisomeric forms, or a mixture of stereoisomeric forms in any ratio, and the physiologically acceptable salts thereof, and the physiologically acceptable solvates of any of them, wherein A is O;

X is chosen from $(C_1-C_6)$-alkanediyl and $(C_1-C_6)$-alkanediyl-oxy;

$R^1$ is chosen from hydrogen and $(C_1-C_4)$-alkyl;

$R^2$ is phenylene which is optionally substituted on one or more ring carbon atoms by identical or different substituents $R^{22}$;

$R^3$ is chosen from $(C_1-C_6)$-alkyl, $(C_3-C_7)$-cycloalkyl-$C_uH_{2u}$— and Het-$C_vH_{2v}$—, wherein u and v are chosen from 1 and 2, or $R^3$ is a residue of a saturated or unsaturated, 3-membered to 7-membered, monocyclic or bicyclic ring which comprises 0, 1 or 2 identical or different ring heteroatoms chosen from N, O and S, wherein one or two of the ring nitrogen atoms can carry a hydrogen atom or a $(C_1-C_4)$-alkyl substituent and one of the ring sulfur atoms can carry one or two oxo groups, and wherein the residue of a ring is optionally substituted on one or more ring carbon atoms by identical or different substituents $R^{31}$;

$R^{22}$ is chosen from halogen, hydroxy, $(C_1-C_4)$-alkyl- and $(C_1-C_4)$-alkyloxy;

$R^{31}$ is chosen from halogen, $(C_1-C_4)$-alkyl, $(C_3-C_7)$-cycloalkyl, hydroxy and $(C_1-C_4)$-alkyloxy;

Het is a residue of a saturated, 4-membered to 6-membered, monocyclic heterocycle which comprises 1 ring heteroatom chosen from O and S and which is bonded via a ring carbon atom, wherein the residue of a heterocycle is optionally substituted by one or more identical or different substituents chosen from fluorine and $(C_1-C_4)$-alkyl;

wherein all cycloalkyl groups, independently of each other and independently of any other substituents, are optionally substituted by one or more identical or different substituents chosen from fluorine and $(C_1-C_4)$-alkyl;

wherein all alkyl, alkanediyl, $C_uH_{2u}$ and $C_vH_{2v}$ groups, independently of each other and independently of any other substituents, are optionally substituted by one or more fluorine substituents.

Another such example are compounds of the formula I, in any of their stereoisomeric forms, or a mixture of stereoisomeric forms in any ratio, and the physiologically acceptable salts thereof, and the physiologically acceptable solvates of any of them, wherein A is O;

X is chosen from $(C_1-C_6)$-alkanediyl and $(C_1-C_6)$-alkanediyloxy;

$R^1$ is chosen from hydrogen and $(C_1-C_4)$-alkyl;

$R^2$ is phenylene which is optionally substituted on one or more ring carbon atoms by identical or different substituents $R^{22}$;

$R^3$ is a residue of a saturated or unsaturated, 3-membered to 7-membered, monocyclic ring which comprises 0 or 1 ring heteroatom chosen from N, O and S, wherein a ring nitrogen atom can carry a hydrogen atom or a $(C_1-C_4)$-alkyl substituent and a ring sulfur atoms can carry one or two oxo groups, and wherein the residue of a ring is optionally substituted on one or more ring carbon atoms by identical or different substituents $R^{31}$;

$R^{22}$ is chosen from halogen, hydroxy, $(C_1-C_4)$-alkyl- and $(C_1-C_4)$-alkyloxy;

$R^{31}$ is chosen from halogen, $(C_1-C_4)$-alkyl, $(C_3-C_7)$-cycloalkyl, hydroxy and $(C_1-C_4)$-alkyloxy;

wherein all cycloalkyl groups, independently of each other and independently of any other substituents, are optionally substituted by one or more identical or different substituents chosen from fluorine and $(C_1-C_4)$-alkyl;

wherein all alkyl and alkanediyl groups, independently of each other and independently of any other substituents, are optionally substituted by one or more fluorine substituents.

Likewise, also with respect to all specific compounds disclosed herein, such as the example compounds which represent embodiments of the invention wherein the various groups and numbers in the general definition of the compounds of the formula I have the specific meanings present in the respective specific compound, it applies that they are a subject of the present invention in any of their stereoisomeric forms and or a mixture of stereoisomeric forms in any ratio, and in the form of their physiologically acceptable salts, and in the form of the physiologically acceptable solvates of any of them. Irrespective thereof whether a specific compound is disclosed herein as a free compound and/or as a specific salt, it is a subject of the invention both in the form of the free compound and in the form of all its physiologically acceptable salts, and if a specific salt is disclosed, additionally in the form of this specific salt, and in the form of the physiologically acceptable solvates of any of them. Thus, a subject of the invention also is a compound of the formula I which is chosen from any one or more of the specific compounds of the formula I disclosed herein, including the example compounds specified below, and the physiologically acceptable salts thereof, and the physiologically acceptable solvates of any of them, wherein the compound of the formula I is a subject of the invention in any of its stereoisomeric forms or a mixture of stereoisomeric forms in any ratio, if applicable. As an example mentioned is a compound of the formula I, or a physiologically acceptable salt thereof, or a physiologically acceptable solvate of any of them, which is chosen from

[2,6-dimethyl-4-(5-phenoxy-oxazolo[5,4-d]pyrimidin-2-yl)-phenoxy]-acetic acid, (E)-3-{4-[5-(2-fFluoro-phenoxy)-oxazolo[5,4-d]pyrimidin-2-yl]-phenyl}-acrylic acid, {4-[5-(2,4-difluoro-phenoxy)-oxazolo[5,4-d]pyrimidin-2-yl]-2,6-dimethyl-phenoxy}-acetic acid, {4-[5-(2,5-difluoro-phenoxy)-oxazolo[5,4-d]pyrimidin-2-yl]-2,6-dimethyl-phenoxy}-acetic acid, {4-[5-(2-fluoro-4-methyl-phenoxy)-oxazolo[5,4-d]pyrimidin-2-yl]-2,6-dimethyl-phenoxy}-acetic acid, {4-[5-(2-fluoro-phenoxy)-oxazolo[5,4-d]pyrimidin-2-yl]-2,6-dimethyl-phenoxy}-acetic acid, 2-{4-[5-(2-fluoro-phenoxy)-oxazolo[5,4-d]pyrimidin-2-yl]-2,6-dimethyl-phenoxy}-propionic acid, {4-[5-(3-chloro-phenoxy)-oxazolo[5,4-d]pyrimidin-2-yl]-2,6-dimethyl-phenoxy}-acetic acid, {4-[5-(3-fluoro-4-methyl-phenoxy)-oxazolo[5,4-d]pyrimidin-2-yl]-2,6-dimethyl-phenoxy}-acetic acid, {4-[5-(5-fluoro-2-methyl-phenoxy)-oxazolo[5,4-d]pyrimidin-2-yl]-2,6-dimethyl-phenoxy}-acetic acid, {4-[5-(4-chloro-phenoxy)-oxazolo[5,4-d]pyrimidin-2-yl]-2,6-dimethyl-phenoxy}-acetic acid,

[4-(5-cyclopentyloxy-oxazolo[5,4-d]pyrimidin-2-yl)-2,6-dimethyl-phenoxy]-acetic acid, {4-[5-(2-fluoro-phenoxy)-oxazolo[5,4-d]pyrimidin-2-yl]-2-methyl-phenoxy}-acetic acid, {4-[5-(2-fluoro-phenoxy)-oxazolo[5,4-d]pyrimidin-2-yl]-phenoxy}-acetic acid, 2-{4-[5-(2-fluoro-phenoxy)-oxazolo[5,4-d]pyrimidin-2-yl]-phenoxy}-2-methyl-propionic acid, 2-{4-[5-(2-fluoro-phenoxy)-oxazolo[5,4-d]pyrimidin-2-yl]-phenoxy}-propionic acid, {4-[5-(2-fluoro-phenoxy)-oxazolo[5,4-d]pyrimidin-2-yl]-2-trifluoromethyl-phenoxy}-acetic acid, 3-{4-[5-(2-fluoro-phenoxy)-oxazolo[5,4-d]pyrimidin-2-yl]-phenyl}-propionic acid, 3-{4-[5-(2-fluoro-phenoxy)-oxazolo[5,4-d]pyrimidin-2-yl]-phenyl}-2-methyl-propionic acid, 4-{4-[5-(2-fluoro-phenoxy)-oxazolo[5,4-d]pyrimidin-2-yl]-phenoxy}-butyric acid, 4-{4-[5-(2-fluoro-phenoxy)-oxazolo[5,4-d]pyrimidin-2-yl]-2,6-dimethyl-phenoxy}-butyric acid, {4-[5-(2-cyclopropyl-ethoxy)-oxazolo[5,4-d]pyrimidin-2-yl]-2,6-dimethyl-phenoxy}-acetic acid, {2,6-dimethyl-4-[5-(3-methyl-butoxy)-oxazolo[5,4-d]pyrimidin-2-yl]-phenoxy}-acetic acid, 2-[2,6-dimethyl-4-(5-{2,4-difluoro-phenoxy}-oxazolo[5,4-d]pyrimidin-2-yl)-phenoxy]-propionic acid, 2-[2,6-dimethyl-4-(5-{2,3-difluoro-phenoxy}-oxazolo[5,4-d]pyrimidin-2-yl)-phenoxy]-propionic acid, 2-[2,6-dimethyl-4-(5-{2,5-difluoro-phenoxy}-oxazolo[5,4-d]pyrimidin-2-yl)-phenoxy]-propionic acid, 2-[2,6-dimethyl-4-(5-{2-fluoro-5-methyl-phenoxy}-oxazolo[5,4-d]pyrimidin-2-yl)-phenoxy]-propionic acid,
2-[2,6-dimethyl-4-(5-{2-fluoro-4-methyl-phenoxy}-oxazolo[5,4-d]pyrimidin-2-yl)-phenoxy]-propionic acid,
2-[2,6-dimethyl-4-(5-{3-fluoro-phenoxy}-oxazolo[5,4-d]pyrimidin-2-yl)-phenoxy]-propionic acid,
2-[2,6-dimethyl-4-(5-{3,5-difluoro-phenoxy}-oxazolo[5,4-d]pyrimidin-2-yl)-phenoxy]-propionic acid,
2-[2,6-dimethyl-4-(5-{3,4-difluoro-phenoxy}-oxazolo[5,4-d]pyrimidin-2-yl)-phenoxy]-propionic acid,
2-[2,6-dimethyl-4-(5-{2-chloro-5-fluoro-phenoxy}-oxazolo[5,4-d]pyrimidin-2-yl)-phenoxy]-propionic acid,
2-[2,6-dimethyl-4-(5-{4-chloro-3-fluoro-phenoxy}-oxazolo[5,4-d]pyrimidin-2-yl)-phenoxy]-propionic acid,
2-[2,6-dimethyl-4-(5-{3-fluoro-4-methyl-phenoxy}-oxazolo[5,4-d]pyrimidin-2-yl)-phenoxy]-propionic acid,
2-[2,6-dimethyl-4-(5-{3-fluoro-6-methyl-phenoxy}-oxazolo[5,4-d]pyrimidin-2-yl)-phenoxy]-propionic acid,
2-[2,6-dimethyl-4-(5-{3-chloro-phenoxy}-oxazolo[5,4-d]pyrimidin-2-yl)-phenoxy]-propionic acid,
2-[2,6-dimethyl-4-(5-{3-chloro-4-fluoro-phenoxy}-oxazolo[5,4-d]pyrimidin-2-yl)-phenoxy]-propionic acid,
2-[2,6-dimethyl-4-(5-{4-chloro-phenoxy}-oxazolo[5,4-d]pyrimidin-2-yl)-phenoxy]-propionic acid,
2-[2,6-dimethyl-4-(5-{4-methyl-phenoxy}-oxazolo[5,4-d]pyrimidin-2-yl)-phenoxy]-propionic acid,
2-[2,6-dimethyl-4-(5-{3-methyl-phenoxy}-oxazolo[5,4-d]pyrimidin-2-yl)-phenoxy]-propionic acid,
2-[2,6-dimethyl-4-(5-{2-methyl-phenoxy}-oxazolo[5,4-d]pyrimidin-2-yl)-phenoxy]-propionic acid,
2-{2,6-dimethyl-4-[5-(pyridin-3-yloxy)-oxazolo[5,4-d]pyrimidin-2-yl]-phenoxy}-propionic acid,
2-{2,6-dimethyl-4-[5-(6-methyl-pyridin-3-yloxy)-oxazolo[5,4-d]pyrimidin-2-yl]-phenoxy}-propionic acid,
{4-[5-(3-fluoro-phenoxy)-oxazolo[5,4-d]pyrimidin-2-yl]-2,6-dimethyl-phenoxy}-acetic acid,
{2,6-dimethyl-4-[5-(3-trifluoromethyl-phenoxy)-oxazolo[5,4-d]pyrimidin-2-yl]-phenoxy}-acetic acid,
[2,6-dimethyl-4-(5-{3-methylphenoxy}-oxazolo[5,4-d]pyrimidin-2-yl)-phenoxy]-acetic acid,
{4-[5-(3-cycthyl-phenoxy)-oxazolo[5,4-d]pyrimidin-2-yl]-2,6-dimethyl-phenoxy}-acetic acid,
{4-[5-(3-chloro-4-fluoro-phenoxy)-oxazolo[5,4-d]pyrimidin-2-yl]-2,6-dimethyl-phenoxy}-acetic acid,
{4-[5-(3-chloro-4-methyl-phenoxy)-oxazolo[5,4-d]pyrimidin-2-yl]-2,6-dimethyl-phenoxy}-acetic acid,
{4-[5-(5-chloro-2-methyl-phenoxy)-oxazolo[5,4-d]pyrimidin-2-yl]-2,6-dimethyl-phenoxy}-acetic acid,
{4-[5-(3-chloro-2-methyl-phenoxy)-oxazolo[5,4-d]pyrimidin-2-yl]-2,6-dimethyl-phenoxy}-acetic acid,
{4-[5-(3-chloro-2-fluoro-phenoxy)-oxazolo[5,4-d]pyrimidin-2-yl]-2,6-dimethyl-phenoxy}-acetic acid,
{4-[5-(5-chloro-2-fluoro-phenoxy)-oxazolo[5,4-d]pyrimidin-2-yl]-2,6-dimethyl-phenoxy}-acetic acid,
{4-[5-(3,4-difluoro-phenoxy)-oxazolo[5,4-d]pyrimidin-2-yl]-2,6-dimethyl-phenoxy}-acetic acid,
{4-[5-(4-fluoro-3-methyl-phenoxy)-oxazolo[5,4-d]pyrimidin-2-yl]-2,6-dimethyl-phenoxy}-acetic acid,
{4-[5-(2,3-difluoro-phenoxy)-oxazolo[5,4-d]pyrimidin-2-yl]-2,6-dimethyl-phenoxy}-acetic acid,
{4-[5-(3,5-difluoro-phenoxy)-oxazolo[5,4-d]pyrimidin-2-yl]-2,6-dimethyl-phenoxy}-acetic acid,
{4-[5-(3-chloro-5-fluoro-phenoxy)-oxazolo[5,4-d]pyrimidin-2-yl]-2,6-dimethyl-phenoxy}-acetic acid,
{4-[5-(3-fluoro-5-trifluoromethyl-phenoxy)-oxazolo[5,4-d]pyrimidin-2-yl]-2,6-dimethyl-phenoxy}-acetic acid,
{4-[5-(3-fluoro-5-methyl-phenoxy)-oxazolo[5,4-d]pyrimidin-2-yl]-2,6-dimethyl-phenoxy}-acetic acid,
{4-[5-(4-fluoro-phenoxy)-oxazolo[5,4-d]pyrimidin-2-yl]-2,6-dimethyl-phenoxy}-acetic acid,
{4-[5-(2-fluoro-5-methyl-phenoxy)-oxazolo[5,4-d]pyrimidin-2-yl]-2,6-dimethyl-phenoxy}-acetic acid,
{4-[5-(2-chloro-5-fluoro-phenoxy)-oxazolo[5,4-d]pyrimidin-2-yl]-2,6-dimethyl-phenoxy}-acetic acid,
{4-[5-(4-chloro-3-fluoro-phenoxy)-oxazolo[5,4-d]pyrimidin-2-yl]-2,6-dimethyl-phenoxy}-acetic acid,
[2,6-dimethyl-4-(5-{4-methylphenoxy}-oxazolo[5,4-d]pyrimidin-2-yl)-phenoxy]-acetic acid,
[2,6-dimethyl-4-(5-{2-methylphenoxy}-oxazolo[5,4-d]pyrimidin-2-yl)-phenoxy]-acetic acid,
{4-[5-(2-chloro-phenoxy)-oxazolo[5,4-d]pyrimidin-2-yl]-2,6-dimethyl-phenoxy}-acetic acid,
{4-[5-(2-chloro-3-trifluoromethyl-phenoxy)-oxazolo[5,4-d]pyrimidin-2-yl]-2,6-dimethyl-phenoxy}-acetic acid,
{4-[5-(2-chloro-5-trifluoromethyl-phenoxy)-oxazolo[5,4-d]pyrimidin-2-yl]-2,6-dimethyl-phenoxy}-acetic acid,
{4-[5-(4-chloro-3-trifluoromethyl-phenoxy)-oxazolo[5,4-d]pyrimidin-2-yl]-2,6-dimethyl-phenoxy}-acetic acid,
{4-[5-(4-fluoro-3-trifluoromethyl-phenoxy)-oxazolo[5,4-d]pyrimidin-2-yl]-2,6-dimethyl-phenoxy}-acetic acid,
{4-[5-(2-fluoro-5-trifluoromethyl-phenoxy)-oxazolo[5,4-d]pyrimidin-2-yl]-2,6-dimethyl-phenoxy}-acetic acid,
{4-[5-(2-fluoro-3-trifluoromethyl-phenoxy)-oxazolo[5,4-d]pyrimidin-2-yl]-2,6-dimethyl-phenoxy}-acetic acid,
{2,6-dimethyl-4-[5-(2-trifluoromethyl-phenoxy)-oxazolo[5,4-d]pyrimidin-2-yl]-phenoxy}-acetic acid,
{2,6-dimethyl-4-[5-(4-trifluoromethyl-phenoxy)-oxazolo[5,4-d]pyrimidin-2-yl]-phenoxy}-acetic acid,
{4-[5-(4-chloro-2-fluoro-phenoxy)-oxazolo[5,4-d]pyrimidin-2-yl]-2,6-dimethyl-phenoxy}-acetic acid,
{4-[5-(2-chloro-4-fluoro-phenoxy)-oxazolo[5,4-d]pyrimidin-2-yl]-2,6-dimethyl-phenoxy}-acetic acid,
{4-[5-(3-methoxy-phenoxy)-oxazolo[5,4-d]pyrimidin-2-yl]-2,6-dimethyl-phenoxy}-acetic acid,
{2,6-dimethyl-4-[5-(3-trifluoromethoxy-phenoxy)-oxazolo[5,4-d]pyrimidin-2-yl]-phenoxy}-acetic acid,
{2,6-dimethyl-4-[5-(3-trifluoromethylsulfanyl-phenoxy)-oxazolo[5,4-d]pyrimidin-2-yl]-phenoxy}-acetic acid,
{4-[5-(indan-5-yloxy)-oxazolo[5,4-d]pyrimidin-2-yl]-2,6-dimethyl-phenoxy}-acetic acid,
{4-[5-(indan-4-yloxy)-oxazolo[5,4-d]pyrimidin-2-yl]-2,6-dimethyl-phenoxy}-acetic acid,
{2,6-dimethyl-4-[5-(naphthalen-2-yloxy)-oxazolo[5,4-d]pyrimidin-2-yl]-phenoxy}-acetic acid,
{2,6-dimethyl-4-[5-(2-methyl-benzothiazol-5-yloxy)-oxazolo[5,4-d]pyrimidin-2-yl]-phenoxy}-acetic acid,
{4-[5-(benzothiazol-6-yloxy)-oxazolo[5,4-d]pyrimidin-2-yl]-2,6-dimethyl-phenoxy}-acetic acid,
{2,6-dimethyl-4-[5-(6-methyl-pyridin-3-yloxy)-oxazolo[5,4-d]pyrimidin-2-yl]-phenoxy}-acetic acid,
{2,6-dimethyl-4-[5-(2-methyl-pyridin-3-yloxy)-oxazolo[5,4-d]pyrimidin-2-yl]-phenoxy}-acetic acid,
{2,6-dimethyl-4-[5-(5-methyl-pyridin-3-yloxy)-oxazolo[5,4-d]pyrimidin-2-yl]-phenoxy}-acetic acid,
{4-[5-(5-chloro-pyridin-3-yloxy)-oxazolo[5,4-d]pyrimidin-2-yl]-2,6-dimethyl-phenoxy}-acetic acid,
{4-[5-(5-fluoro-pyridin-3-yloxy)-oxazolo[5,4-d]pyrimidin-2-yl]-2,6-dimethyl-phenoxy}-acetic acid,
{2,6-dimethyl-4-[5-([1,2,5]thiadiazol-3-yloxy)-oxazolo[5,4-d]pyrimidin-2-yl]-phenoxy}-acetic acid,
{4-[5-(Isothiazol-3-yloxy)-oxazolo[5,4-d]pyrimidin-2-yl]-2,6-dimethyl-phenoxy}-acetic acid, {2,6-dimethyl-4-[5-(5-trifluoromethyl-thiophen-3-yloxy)-oxazolo[5,4-d]pyrimidin-2-yl]-phenoxy}-acetic acid, {2,6-dimethyl-4-[5-(thiazol-2-ylsulfanyl)-oxazolo[5,4-d]pyrimidin-2-yl]-phenoxy}-acetic acid, {2,6-dimethyl-4-[5-(4-methyl-thiazol-2-ylsulfanyl)-oxazolo[5,4-d]pyrimidin-2-yl]-phenoxy}-acetic acid, {4-[5-(1,1-dioxo-tetrahydro-thiophen-3-ylsulfanyl)-oxazolo[5,4-d]pyrimidin-2-yl]-2,6-dimethyl-phenoxy}-acetic acid, and {4-[5-(2,5-dimethyl-furan-3-ylsulfanyl)-oxazolo[5,4-d]pyrimidin-2-yl]-2,6-dimethyl-phenoxy}-acetic acid, wherein a compound such as 2-{4-[5-(2-fluoro-phenoxy)-oxazolo[5,4-d]pyrimidin-2-yl]-2,6-dimethyl-phenoxy}-propionic acid or 2-{4-[5-(2-fluoro-phenoxy)-oxazolo[5,4-d]pyrimidin-2-yl]-phenoxy}-propionic acid, for example, which can be present in S configuration or R configuration, is a subject of the invention in S configuration and in R configuration and as a mixture of the enantiomeric forms in any ratio.

Another subject of the present invention are processes for the preparation of the compounds of the formula I and their salts and solvates, by which the compounds are obtainable and which are outlined in the following. In one process, a compound of the formula II is reacted with a compound of the formula III to give a compound of the formula I,

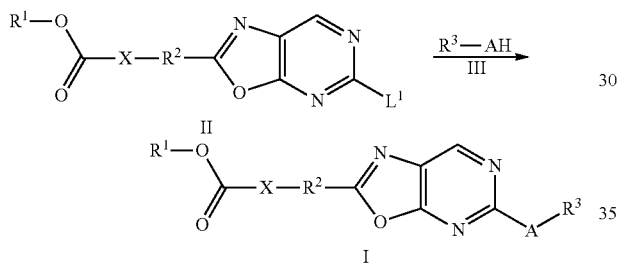

wherein the groups A, X, $R^1$, $R^2$ and $R^3$ in the compounds of the formulae II and III are defined as in the compounds of the formula I and additionally functional groups can be present in protected form or in the form of a precursor group which is later converted into the final group. The group $L^1$ in the compounds of the formula II is a leaving group which can be replaced in a nucleophilic aromatic substitution reaction, such as a halogen atom, for example chlorine or bromine, or a sulfoxide group or a sulfone group, for example a group of the formula —S(O)-Alk or —S(O)$_2$-Alk wherein Alk is a ($C_1$-$C_4$)-alkyl group, for example methyl or ethyl.

The reaction of the compounds of the formulae II and III is a nucleophilic aromatic substitution reaction at the carbon atom in the 5-position of oxazolo[5,4-d]pyrimidine ring, i.e. in the pyrimidine moiety, and can be carried out under standard conditions for such reactions which are well known to a person skilled in the art. Generally the reaction is carried out in an inert solvent, for example a hydrocarbon or chlorinated hydrocarbon such as benzene, toluene, xylene, chlorobenzene, dichloromethane, chloroform or dichloroethane, an ether such as tetrahydrofuran (THF), dioxane, dibutyl ether, diisopropyl ether or 1,2-dimethoxyethane (DME), a ketone such as acetone or butan-2-one, an ester such as ethyl acetate or butyl acetate, a nitrile such acetonitrile, an amide such as N,N-dimethylformamide (DMF), N,N-dimethylacetamide (DMA) or N-methylpyrrolidin-2-one (NMP), or a mixture of solvents, at temperatures from about 20° C. to about 160° C., for example at temperatures from about 40° C. to about 100° C., depending on the particulars of the specific case. Generally it is favorable for enhancing the nucleophilicity of the compound of the formula III to add a base, for example a tertiary amine, such as triethylamine, ethyldiisopropylamine or N-methylmorpholine, or an inorganic base such as an alkaline metal hydride, hydroxide, carbonate or hydrogencarbonate like sodium hydride, sodium hydroxide, potassium hydroxide, sodium carbonate, potassium carbonate, cesium carbonate or sodium hydrogencarbonate, or an alkoxide or amide such as sodium methoxide, sodium ethoxide, potassium methoxide, potassium tert-butoxide, sodium amide or lithium diisopropylamide. A compound of the formula III can also be treated with a base and converted into a salt separately before the reaction with the compound of the formula II.

The starting compounds of the formulae II and III can be obtained by procedures described in the literature or analogously to procedures described in the literature, and in many cases are commercially available. For example, the compounds of the formula II can be obtained by reacting a 5-amino-pyrimidine derivative of the formula IV with an activated carboxylic acid derivative of the formula V to give a compound of the formula VI, cyclizing the latter compound with formation of the oxazolo[5,4-d]pyrimidine ring system to give a compound of the formula VII, and introducing the moiety $R^{10}$—C(O)—X— into the compound of the formula VII by reaction with a compound of the formula VIII to give a compound of the formula IX which can already be a compound of the formula II depending on the meaning of R' and $L^1$, and optionally modifying the group R' in the compound of the formula IX to give a compound of the formula II.

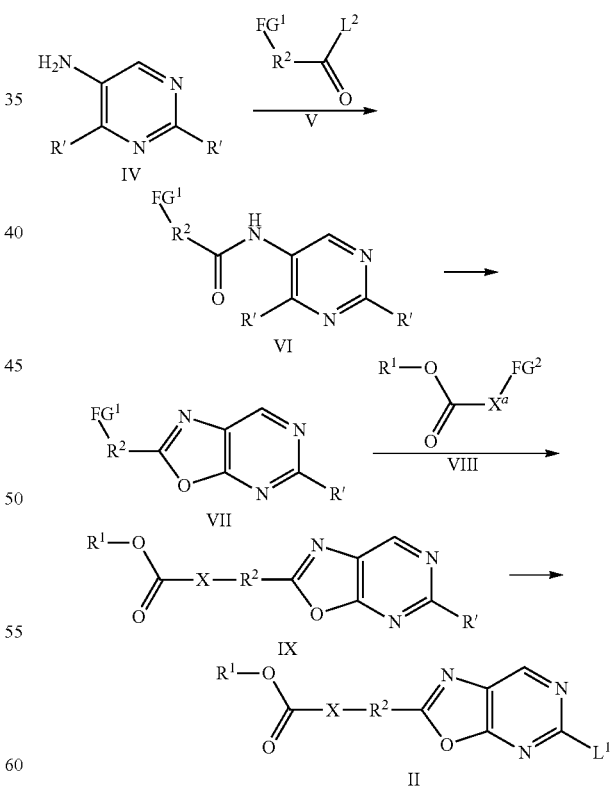

The groups X, $R^1$ and $R^2$ in the compounds of the formulae V, VI, VIII and IX are defined as in the compounds of the formula I and additionally functional groups can be present in protected form or in the form of a precursor group which is later converted into the final group. The group $X^a$ in the compounds of the formula VIII is defined as the group X in the compounds of the formula I, or comprises a part of the group X in the desired compound of the formula II, such that after the reaction of the compounds of the formulae VII and VIII the group $X^a$ and any parts of the groups $FG^1$ and $FG^2$ remaining in the compound of the formula IX together form the desired group X. For example, in case the group X is an alkanediyl-oxy group, the group $X^a$ in the compound of the formula VIII can be the desired alkanediyl-oxy group and the group $FG^2$ can be a hydrogen atom attached to the oxygen atom, or the group $X^a$ can be the alkanediyl part, the group $FG^2$ is a leaving group, and the group $FG^1$ in the compound of the formula VII is a hydroxy group the oxygen atom of which together with the alkanediyl part then forms the desired alkanediyl-oxy group after alkylation of the compound of the formula VII with the compound of the formula VIII.

The groups $FG^1$ and $FG^2$ in the compounds of the formulae V, VI, VII and VIII are functional groups suitable for the type of coupling used to form the desired group X from the group $X^a$ and any part of the groups $FG^1$ and $FG^2$ remaining in the compound of the formula IX. For example, if the group $X^a$ is attached to the group $R^2$ or to an atom in the group $FG^1$, such as an oxygen atom in a hydroxy group representing $FG^1$ as mentioned afore, via a nucleophilic substitution reaction, $FG^2$ can be a leaving group such as a halogen atom like as chlorine, bromine or iodine or a sulfonyloxy group like methanesulfonyloxy, trifluoromethanesulfonyloxy or toluenesulfonyloxy. If the group $X^a$ is attached to the group $R^2$ via a transition metal-catalyzed reaction, $FG^2$ can be a leaving group such as a boronic acid, boronic acid ester, dialkyl borane or stannane group, and in this case $FG^1$ can be halogen. $FG^2$ can also be a hydrogen atom on a carbon atom being part of a double bond in an alkenediyl group representing $X^a$ if a Heck reaction is used for attaching $X^a$ to $R^2$, and this case $FG^1$ can be halogen. If a Wittig reaction or Wittig-Horner reaction is used for attaching $X^a$ to $R^2$, $FG^2$ can be a phosphonio group such as triphenylphosphonio or a phosphonyl group such as diethyl phosphonyl, and the compound of the formula XIV be a phosphonium salt or a phosphonic acid ester, and in this case $FG^1$ can be an aldehyde group —C(O)—H or ketone group —C(O)-alkyl, and vice versa. Generally, the group $FG^1$ is present on the carbon atom in the phenylene group or heterocyclic group representing $R^2$ which in the compounds of the formulae IX, II and I carries the group X. The group $FG^1$ in the compounds of the formulae V, VI and VII can also be present in protected form or in the form of a precursor group which is later converted into the group which in the compound of the formula VII reacts with the compound of the formula VIII. For example, a hydroxy group representing $FG^1$ in the compound of the formula VII can be present in the compounds of the formulae V and VI in protected form, for example in the form of an etherified hydroxy group such as a benzyl ether or an alkyl ether like a methyl ether. Such ethers can be cleaved by using methods well known to a person skilled in the art. A summary of methods for the removal of protecting groups can be found in the literature, for example in P. J. Kocienski, Protecting Groups (Thieme Verlag, 1994) or T. W. Greene and P. G. M. Wuts, Protective Groups in Organic Synthesis (John Wiley & Sons, 1999).

The group $L^2$ in the compounds of the formula V is a nucleophilically substitutable leaving group and can in particular be a halogen atom, such as chlorine or bromine, and the compound of the formula V can thus be a carboxylic acid halide. $L^2$ can also be a group of the formula $FG^1$-$R^2$—C(O)—O and the compound of the formula V can thus be a carboxylic acid anhydride, for example. The groups R' in the compounds of the formulae IV, VI, VII and IX can be a hydroxy group or a halogen atom, such as chlorine or bromine. Compounds occurring in the synthesis of the compounds of the formula I, such as the compound of the formula IV, may also present in another tautomeric form, for example in the keto form in case the groups R' in the compound of the formula IV are hydroxy groups. Compounds occurring in the synthesis of the compounds of the formula I, including starting compounds, intermediates and products, can also be employed or obtained in the form of a salt.

The reaction of the compounds of the formulae IV and V can be carried out under standard conditions for the acylation of an amine with an activated carboxylic acid derivative like an acid halide or anhydride. Generally the reaction is carried out in an inert solvent, for example a hydrocarbon or chlorinated hydrocarbon such as benzene, toluene, xylene, chlorobenzene, dichloromethane, chloroform or dichloroethane, an ether such as THF, dioxane, dibutyl ether, diisopropyl ether or DME, a ketone such as acetone or butan-2-one, an ester such as ethyl acetate or butyl acetate, or water, or a mixture of solvents, at temperatures from about −10° C. to about 40° C., for example at temperatures from about 0° C. to about 30° C. Generally the reaction is carried out with addition of a base, for example a tertiary amine, such as triethylamine, ethyldiisopropylamine or N-methylmorpholine, or an inorganic base such as an alkaline metal hydroxide, carbonate or hydrogencarbonate like sodium hydroxide, potassium hydroxide, sodium carbonate, potassium carbonate or sodium hydrogencarbonate.

In case the group R' in the compound of the formula VI is hydroxy, the cyclization of the compound of the formula VI to the compound of the formula VII can favorably be carried out in the presence of a halogenating agent such as a phosphorus halide, like phosphorus pentachloride or phosphorus oxychloride or a mixture thereof, in an inert solvent, for example a hydrocarbon or chlorinated hydrocarbon such as benzene, toluene, xylene, chlorobenzene, dichloromethane, chloroform or dichloroethane, at temperatures from about 20° C. to about 100° C., for example temperatures from about 50° C. to about 80° C. In case the group $R^1$ in the compound of the formula VI is halogen such as chlorine, the cyclization of the compound of the formula VI to the compound of the formula VII can be carried out thermally, for example by heating the compound of the formula VI in an inert solvent such as a hydrocarbon or chlorinated hydrocarbon, for example toluene, xylene or chlorobenzene, or an amide, for example DMF, DMA or NMP, or a nitrile, for example acetonitrile, to temperatures from about 100° C. to about 200° C., for example to temperatures from about 120° C. to about 180° C., optionally under pressure, and optionally in the presence of a base, such as a tertiary amine, for example triethylamine, ethyldiisopropylamine or N-methylmorpholine, or an inorganic base, for example an alkaline metal hydroxide, carbonate or hydrogencarbonate like sodium hydroxide, potassium hydroxide, sodium carbonate, potassium carbonate or sodium hydrogencarbonate. The thermal cyclization can favorably be performed in a microwave reactor.

The coupling of compounds of the formula VIII with compounds of the formula VII can be carried out via reactions of various types as already indicated above, for example via an alkylation reaction. For example, if the group $R^2$ carries a hydroxy group representing $FG^1$, it can be alkylated using a compound of formula VIII in which $FG^2$ is a leaving group suitable for nucleophilic substitution reactions such as a halogen atom like chlorine, bromine or iodine, or a sulfonyloxy group like methanesulfonyloxy or toluenesulfonyloxy. The nucleophilic substitution reaction at the carbon atom in the compound of the formula VIII carrying the group $FG^2$ can be carried out under standard conditions for such reactions which are well known to a person skilled in the art. Generally the reaction is carried out in an inert solvent, for example a hydrocarbon or chlorinated hydrocarbon such as benzene, toluene, xylene, chlorobenzene, dichloromethane, chloroform or dichloroethane, an ether such as THF, dioxane, dibutyl ether, diisopropyl ether or DME, an alcohol such as methanol, ethanol or isopropanol, a ketone such as acetone or butan-2-one, an ester such as ethyl acetate or butyl acetate, a nitrile such acetonitrile, an amide such as N,N-dimethylformamide or N-methylpyrrolidin-2-one, or a mixture of solvents, at temperatures from about 20° C. to about 100° C., for example at temperatures from about 40° C. to about 80° C., depending on the particulars of the specific case. Generally it is favorable for enhancing the nucleophilicity of the compound of the formula XIII and/or binding an acid which is liberated during the reaction, to add a base, for example a tertiary amine, such as triethylamine, ethyldiisopropylamine or N-methylmorpholine, or an inorganic base such as an alkaline metal hydride, hydroxide, carbonate or hydrogencarbonate like sodium hydride, sodium hydroxide, potassium hydroxide, sodium carbonate, potassium carbonate, cesium carbonate or sodium hydrogencarbonate, or an alkoxide or amide such as sodium methoxide, sodium ethoxide, potassium methoxide, potassium tert-butoxide, sodium amide or lithium diisopropylamide. A compound of the formula VII in which $FG^1$ is hydroxy can also be treated with a base and converted into a salt separately before the reaction with the compound of the formula VIII. Besides by reaction with a compound of the formula VIII in which $FG^2$ is a leaving group as indicated, a compound of the formula VII in which $FG^1$ is hydroxy can also be converted into a compound of the formula IX by reaction with the respective alcohol, i.e. with a compound of the formula VIII in which $FG^2$ is hydroxy, under the conditions of the Mitsunobu reaction in the presence of an azodicarboxylate such as diethyl azodicarboxylate or diisopropyl azodicarboxylate and a phosphine such as triphenylphosphine or tributylphosphine in an inert aprotic solvent, for example an ether such as THF or dioxane (cf. O. Mitsunobu, Synthesis (1981), 1-28). The coupling of compounds of the formula VIII with compounds of the formula VII via a transition metal-catalyzed reaction can be performed under the conditions of palladium-catalyzed cross coupling reactions like the Heck, Stille or Suzuki coupling reaction (c. f. A. de Meijere and F. Diederich (Eds.), Metal-Catalyzed Cross-Coupling Reactions (Wiley-VCH, 2004)).

The compound of the formula IX can already be a compound of the formula II and employed in the reaction with the compound of the formula III, if it has been obtained from a compound of the formula VI in which R' is halogen, such as chlorine, and the halogen atom in the cyclization product has not been replaced in the course of the synthesis, for example with a hydroxy group during work-up, or if it has been obtained from a compound of the formula VI in which R' is hydroxy, and concomitantly with the cyclization the second hydroxy group in the compound of the formula VI is halogenated, for example replaced with a chlorine atom as may occur during the cyclization by means of a phosphorus halide. If a compound of the VII in which R' is hydroxy, is obtained as cyclization product, the hydroxy group in the compound of the formula IX can be converted into a leaving group under standard conditions, for example into a halogen atom such as a chlorine atom by treatment with a halogenating agent such as a phosphorus halide, or into a sulfonyloxy group as indicated above by treatment with a sulfonyl chloride or sulfonic acid anhydride. Depending on the particulars of the specific case, such as the reactivity of the specific compound of the formula III which is to be reacted with the compound of the formula II, it can also be advantageous to modify the group R' in a compound of the formula IX, even though it already is a leaving group. For example, a compound of the formula IX in which R' is halogen, such as chlorine, can be converted into a compound of the formula II in which $L^1$ is the group —S(O)$_2$-Alk and which is then reacted with a compound of the formula III, by treatment with an alkanesulfinic acid of the formula Alk-S(O)—OH, wherein Alk is $(C_1-C_4)$-alkyl. Such a conversion is generally carried out in the presence of a base, such as an alkaline metal hydride, hydroxide, carbonate or hydrogencarbonate like sodium hydride, sodium hydroxide, potassium hydroxide, sodium carbonate, potassium carbonate, cesium carbonate or sodium hydrogencarbonate, in an inert solvent, such as a hydrocarbon or chlorinated hydrocarbon like benzene, toluene, xylene, chlorobenzene, dichloromethane, chloroform or dichloroethane, an ether such as THF, dioxane, dibutyl ether, diisopropyl ether or DME, an amide such as DMF or NMP, or a mixture of solvents, at temperatures from about 20° C. to about 150° C., for example at temperatures from about 50° C. to about 120° C. An alkanesulfinic acid can also be treated with a base and converted into a salt separately before the reaction with the compound of the formula IX.

The sequence of steps in the preparation of the compounds of the formula I can also be changed and, for example, the group -A-$R^3$ introduced at an earlier by reaction of a compound of the formula VII in which R' is a leaving group, or by reaction of a compound of the formula VII which contains the group $L^1$ defined as above which has been obtained from a compound of the formula VII by conversion of the group R' into the group $L^1$, with a compound of the formula III, and the obtained product reacted with a compound of the formula VIII to give compound of the formula I. The explanations given above for the reaction of the compound of the formulae II and III and the reaction of the compounds of the formulae VII and VIII apply correspondingly to respective reaction steps in such synthesis of the compounds of the formula I.

Further compounds of the formula I can be obtained from suitable compounds prepared according to the above-described processes by functionalization or modification of contained functional groups according to standard procedures, for example by esterification, amidation, hydrolysis, etherification, alkylation, acylation, sulfonylation, reduction, oxidation, conversion into salts, and others. For example, a hydroxy group, which may be liberated from an ether group by ether cleavage, for example by means of boron tribromide, or from a protected hydroxy group by deprotection, can be esterified to give a carboxylic acid ester or a sulfonic acid ester, or etherified. Etherifications of hydroxy groups can favorably be performed by alkylation with the respective halogen compound, for example a bromide or iodide, in the presence of a base, for example an alkaline metal carbonate such potassium carbonate or cesium carbonate in an inert solvent, for example an amide like DMF or NMP or a ketone like acetone or butan-2-one, or with the respective alcohol under the conditions of the Mitsunobu reaction referred to above. A hydroxy group can be converted into a halide by treatment with a halogenating agent. A halogen atom can be replaced with a variety of groups in a substitution reaction which may also be a transition-metal catalyzed reaction. A nitro group can be reduced to an amino group, for example by catalytic hydrogenation. An amino group can be modified under standard conditions for alkylation, for example by reaction with a halogen compound or by reductive amination of a carbonyl compound, or for acylation or sulfonylation, for example by reaction with a reactive carboxylic acid derivative, like an acid chloride or anhydride or a sulfonic acid chloride, or with an activated carboxylic acid which may be obtained from the carboxylic acid by treatment with a coupling agent like N,N'-carbonyldiimidazole (CDI), a carbodiimide such as 1,3-dicyclohexylcarbodiimide (DCC) or 1-(3-dimethylaminopropyl)-3-ethylcarbodiimide hydrochloride (EDC), O-(7-azabenzotriazol-1-yl)-N,N,N',N'-tetramethyluronium hexafluorophosphate (HATU), O-(cyano(ethoxycarbonyl)methyleneamino)-N,N,N',N'-tetramethyluronium tetrafluoroborate (TOTU), or [(benzotriazol-1-yloxy)-dimethylamino-methylene]-dimethyl-ammonium tetrafluoroborate (TBTU), for example. A carboxylic ester group can be hydrolyzed under acidic or basic conditions to give a carboxylic acid. A carboxylic acid group can be activated or converted into a reactive derivative as mentioned afore and reacted with an alcohol or an amine or ammonia to give an ester or amide. A primary amide can be dehydrated to give a nitrile. A sulfur atom, for example in an alkyl-S— group or in a heterocyclic ring, can be oxidized with a peroxide like hydrogen peroxide or a peracid to give a sulfoxide moiety S(O) or a sulfone moiety $S(O)_2$. A carboxylic acid group, carboxylic acid ester group and a ketone group can be reduced to an alcohol, for example by means of a complex hydride such as lithium aluminium hydride, lithium borohydride or sodium borohydride. A compound of the formula I or an intermediate such as a compound of the formula II, which contains a double bond or a triple bond in the group X, which can be readily obtained via a transition metal-catalyzed coupling reaction from a compound of the formula XIV containing a double or triple bond in the group $X^a$ and a compound of the formula XIII as outlined above, can be converted into a compound in which X is a saturated group, by hydrogenation in the presence of hydrogenation catalyst such as a palladium catalyst.

All reactions used in the above-described syntheses of the compounds of the formula I are per se well known to the skilled person and can be carried out under standard conditions according to, or analogously to, procedures described in the literature, for example in Houben-Weyl, Methoden der Organischen Chemie (Methods of Organic Chemistry) (Thieme-Verlag, Stuttgart), or Organic Reactions (John Wiley & Sons, New York). If desired, the obtained compounds of the formula I, as well as any intermediate compounds, can be purified by customary purification procedures, for example by recrystallization or chromatography. As already mentioned, all starting compounds and intermediates employed into the above-described syntheses which contain an acidic or basic group, can also be employed in the form of salts, and all intermediates and final target compounds can also be obtained in the form of salts. As likewise mentioned above, depending on the circumstances of the specific case, in order to avoid an unwanted course of a reaction or side reactions during the synthesis of a compound it can generally be necessary or advantageous to temporarily block functional groups by introducing protective groups and deprotect them at a later stage of the synthesis, or to introduce functional groups in the form of precursor groups which later are converted into the desired functional groups. As examples of protecting groups amino-protecting groups may be mentioned which can be acyl groups or alkyloxycarbonyl groups, for example a tert-butyloxycarbonyl group (=Boc) which can be removed by treatment with trifluoroacetic acid (=TFA), a benzyloxycarbonyl group which can be removed by catalytic hydrogenation, or a fluoren-9-ylmethoxycarbonyl group which can be removed by treatment with piperidine, and protecting groups of carboxylic acid groups which can be protected as ester groups, such as tert-butyl esters which can be deprotected by treatment with trifluoroacetic acid, or benzyl esters which can be deprotected by catalytic hydrogenation. As an example of a precursor group the nitro group may be mentioned which can be converted into an amino group by reduction, for example by catalytic hydrogenation. Such synthesis strategies, and protective groups and precursor groups which are suitable in a specific case, are known to the skilled person.

Another subject of the present invention are the novel starting compounds and intermediates occurring in the synthesis of the compounds of the formula I, including the compounds of the formulae II, III, IV, V, VI, VII, VIII and IX, wherein A, X, $X^a$, $R^1$, $R^2$, $R^3$, R', $FG^1$, $FG^2$, $L^1$ and $L^2$ are defined as above, in any of their stereoisomeric forms or a mixture of stereoisomeric forms in any ratio, and their salts, and solvates of any of them, and their use as intermediates. The invention also includes all tautomeric forms of the said intermediates and starting compounds. All explanations given above and embodiments specified above with respect to the compounds of the formula I apply correspondingly to the said intermediates and starting compounds. A subject of the invention are in particular the novel specific starting compounds and intermediates disclosed herein. Independently thereof whether they are disclosed as a free compound and/or as a specific salt, they are a subject of the invention both in the form of the free compounds and in the form of their salts, and if a specific salt is disclosed, additionally in the form of this specific salt, and in the form of solvates of any of them.

The compounds of the formula I are useful pharmacologically active compounds which modulate the Edg-1 receptor and more specifically act as efficacious Edg-1 agonists, and which can be employed as pharmaceuticals, or as active ingredients of pharmaceutical compositions or medicaments, and used for the treatment of various diseases. The Edg-1 agonistic action also includes the possibility of a functional impairment of Edg-1 receptor signaling due to tachyphylaxis or receptor desensitization which is desirable in the treatment of certain diseases. The efficacy of the compounds of the formula I can be demonstrated in the pharmacological test described below and other tests which are known to a person skilled in the art, for example in the mouse model of renoprotection after ischemia-reperfusion described in A. S. Awad et al., Am. J. Physiol. Renal Physiol. 290 (2006), F1516-F1524, or in the mouse model of atherosclerosis described in J.-R. Nofer et al., Circulation 115 (2007), 501-508. In the context of the present invention, treatment of diseases is understood as comprising both therapy, including alleviation and cure, of diseases or disease symptoms and prevention or prophylaxis of diseases or disease symptoms. For example, in patients who on account of their disease history are susceptible to myocardial infarction, or to asthmatic attacks, by means of a preventive or prophylactic medicinal treatment the occurrence or re-occurrence of a myocardial infarction, or of asthmatic disease symptoms, respectively, can be prevented or their extent or sequelae decreased. The diseases or disease symptoms can be acute or chronic. Diseases which can be treated with the compounds of the formula I, include cardiovascular diseases, coronary heart disease, coronary artery disease, stable and unstable angina pectoris, Prinzmetal angina (spasm), acute coronary syndrome, myocardial infarction, cardiac ischemia and/or reperfusion injury including cardiac ischemia and/or reperfusion injury during cardiac surgery or transplantation, cardiac insufficiency, heart failure including systolic heart failure, diastolic heart failure and heart failure with preserved ejection fraction (=HF-PEF), cardiomyopathy, stroke, thrombosis, atherosclerosis, endothelial dysfunction, peripheral arterial occlusive disease (=PAOD=peripheral arterial disease=PAD), restenosis, vasculopathy including transplant vasculopathy, endothelial damage after PTCA (=percutaneous transluminal coronary angioplasty), hypertension including systolic hypertension, pulmonary hypertension and portal hypertension, vascular remodeling, vascular permeability disorders, and edema including edema formation after surgery or due to drug treatment, for example. The compounds of the formula I can also be used in the treatment, including therapy and prevention, of diabetes, diabetic complications, diabetic cardiomyopathy, diabetic vasculopathy, retinopathy, renal diseases, nephropathy, renal failure including acute renal failure, renal ischemia and/or renal reperfusion injury, respiratory diseases, asthma bronchiale, pulmonary edema, wound healing disorders, inflammatory diseases, rheumatoid arthritis, sepsis, autoimmune diseases, multiple sclerosis, neurodegenerative diseases, CNS injury, spinal chord injury, pain, and cancer, for example. The compounds of the formula I can further be used for modulating angiogenesis, arteriogenesis, vasculogenesis, lymphangiogenesis and vascular maturation, for modulating lymphocyte homing, for modulating stem cell and progenitor cell mobilization, migration, differentiation and homing, for example by treating stem or progenitor cells ex vivo with a compound of the formula I, for modulating immunosuppression including immunosuppression after transplantation, for example. Additionally, the compounds of the formula I can be used for vascular stabilization, for neuronal repair, for cytoprotection, for example in combination with a chemotherapy or after radiation, for renoprotection and for cardioprotection, for example. Other uses of the compounds of the formula I are the improvement of cell cultures, for example as a growth factor or survival factor surrogate for supplementing or replacing serum such as fetal calf serum, for example, and the use in regenerative medicine and cell-based therapy, including the use in stem cell or progenitor cell culture, cellular assays, preparation of primary cells including stem cells, tissue culture and the preservation of cells, tissues and organs and their viability, for example for improving cell-based repair, stem cell or progenitor cell therapy, or tissue or organ transplantation.

Another subject of the present invention thus is a compound of the formula I, in any of its stereoisomeric forms, or a mixture of stereoisomeric forms in any ratio, or a physiologically acceptable salt thereof, or a physiologically acceptable solvate of any of them, for use as a pharmaceutical. Another subject is a pharmaceutical composition, or a medicament, comprising at least one compound of the formula I, in any of its stereoisomeric forms, or a mixture of stereoisomeric forms in any ratio, and/or a physiologically acceptable salt thereof, or a physiologically acceptable solvate of any of them, and a pharmaceutically acceptable carrier, i.e. one or more pharmaceutically acceptable carrier substances and/or additives. A subject of the invention also is a compound of the formula I, in any of its stereoisomeric forms, or a mixture of stereoisomeric forms in any ratio, or a physiologically acceptable salt thereof, or a physiologically acceptable solvate of any of them, for use in the treatment of a disease associated with the Edg-1 receptor, in particular a disease which can be treated by an agonistic action on the Edg-1 receptor or in which an agonistic action on the Edg-1 receptor is desired, for example cardiovascular diseases, atherosclerosis, heart failure, peripheral arterial occlusive disease, renal diseases, inflammatory diseases, vascular permeability disorders, diabetes, respiratory diseases, autoimmune diseases, multiple sclerosis, cancer, or any other disease mentioned above or below herein, or for use in cardioprotection, renoprotection or cytoprotection or for any other use mentioned above or below herein. A subject of the invention also is the use of a compound of the formula I in any of its stereoisomeric forms, or a mixture of stereoisomeric forms in any ratio, or a physiologically acceptable salt thereof, or a physiologically acceptable solvate of any of them, for the manufacture of a medicament for the treatment of a disease associated with the Edg-1 receptor, in particular a disease which can be treated by an agonistic action on the Edg-1 receptor or in which an agonistic action on the Edg-1 receptor is desired, for example cardiovascular diseases, atherosclerosis, heart failure, peripheral arterial occlusive disease, renal diseases, inflammatory diseases, vascular permeability disorders, diabetes, respiratory diseases, autoimmune diseases, multiple sclerosis, cancer, or any other disease mentioned above or below herein, or for cardioprotection, renoprotection or cytoprotection or for any other use mentioned above or below herein. A subject of the invention also is a method for the treatment of a disease associated with the Edg-1 receptor, in particular a disease which can be treated by an agonistic action on the Edg-1 receptor or in which an agonistic action on the Edg-1 receptor is desired, for example cardiovascular diseases, atherosclerosis, heart failure, peripheral arterial occlusive disease, renal diseases, inflammatory diseases, vascular permeability disorders, diabetes, respiratory diseases, autoimmune diseases, multiple sclerosis, cancer, or any other disease mentioned above or below herein, or for cardioprotection, renoprotection or cytoprotection or for any other use mentioned above or below herein, comprising administering to a patient in need thereof a pharmacologically effective dose of compound of the formula I in any of its stereoisomeric forms, or a mixture of stereoisomeric forms in any ratio, or a physiologically acceptable salt thereof, or a physiologically acceptable solvate of any of them. A subject of the present invention also is the use of a compound of the formula I in any of its stereoisomeric forms, or a mixture of stereoisomeric forms in any ratio, or a physiologically acceptable salt thereof, or a physiologically acceptable solvate of any of them, as an additive in the culture, the handling or the preservation of cells, tissues or organs, for example during organ transport for transplantation purposes, or in stem cell or progenitor cell culture, or in scientific experiments including assays and pharmacological tests in which human or animal cells, tissues or organs are used.

The compounds of the formula I can also be used in combination with other pharmacologically active compounds, or pharmaceuticals, in particular with compounds which are able to enhance the favorable physiological effect of the compounds according to formula I, or with compounds which cause any undesired side effect which can be prevented or attenuated by the compounds of the formula I. Examples of such other compounds include statins, HDL (high density lipoprotein) enhancer, cytostatics, PPAR gamma (peroxisome proliferator-activated receptor subtype gamma) agonists, ACE/NEP (angiotensin converting enzyme/neutral endopeptidase) inhibitors and factor Xa inhibitors.

The compounds of the formula I, optionally in combination with other pharmacologically active compounds, can be administered to animals, in particular to mammals including humans, as pharmaceuticals by themselves, in mixtures with one another, or in the form of pharmaceutical compositions. The administration can be carried out orally, for example in the form of tablets, film-coated tablets, sugar-coated tablets, granules, hard and soft gelatin capsules, solutions including aqueous, alcoholic and oily solutions, juices, drops, syrups, emulsions or suspensions, rectally, for example in the form of suppositories, or parenterally, for example in the form of solutions for subcutaneous, intramuscular or intravenous injection or infusion, in particular aqueous solutions. Other suitable administration forms are, for example, percutaneous or topical administration, for example in the form of ointments, creams, tinctures, sprays, powders or transdermal therapeutic systems, or inhalative administration, for example in the form of nasal sprays or aerosol mixtures, or forms such as microcapsules, implants or rods. The compounds of the formula I can additionally be used in modes of local drug delivery, for example in coated stents for preventing or reducing in-stent restenosis or by applying them locally by means of a catheter. The appropriate administration form depends, among others, on the disease to be treated and on its severity.

The amount of a compound of the formula I and/or its physiologically acceptable salts and/or solvates present in the pharmaceutical compositions normally ranges from about 0.2 to about 800 mg, for example from about 0.5 to about 500 mg, for example from about 1 to about 200 mg, per unit dose, but depending on the type of the pharmaceutical composition it may also be higher. The pharmaceutical compositions usually comprise from about 0.5 to about 90 percent by weight of the compound of the formula I and/or its physiologically acceptable salts and/or solvates. The production of the pharmaceutical compositions can be carried out in a manner known per se. To this end, one or more compounds of the formula I and/or their physiologically acceptable salts and/or solvates together with one or more solid or liquid pharmaceutical carrier substances, or vehicles, and/or additives, or auxiliary substances, and, if a combination medicament is desired, other pharmacologically active compounds having therapeutic or prophylactic action are brought into a suitable form for administration and dosage which can be used in human or veterinary medicine. As carrier substances and additives, suitable organic and inorganic substances can be used which do not react in an undesired manner with the compounds of the formula I or their physiologically acceptable salts or solvates. As examples of types of additives which can be contained in the pharmaceutical compositions and medicaments, lubricants, preservatives, thickeners, stabilizers, disintegrants, wetting agents, agents for achieving a depot effect, emulsifiers, salts, for example for influencing the osmotic pressure, buffer substances, colorants, flavorings and aromatic substances may be mentioned. Examples of carrier substances and additives are water, physiologically sodium chloride solution, vegetable oils, waxes, alcohols such as ethanol, isopropanol, 1,2-propanediol, benzyl alcohols or glycerol, polyols, mannitol, polyethylene glycols, polypropylene glycols, glycerol triacetate, polyvinylpyrrolidone, gelatin, cellulose, carbohydrates such as lactose, glucose, saccharose or starch like corn starch, stearic acid and its salts such as magnesium stearate, talc, lanolin, petroleum jelly, or mixtures thereof, for example mixtures of water with one or more organic solvents such as mixtures of water with alcohols. The compounds of the formula I and their physiologically acceptable salts and solvates can also be lyophilized and the obtained lyophilisates used for the production of injectable compositions, for example. For example for topical application, also liposomal compositions are suitable.

The dosage of a compound of the formula I and/or a physiologically acceptable salt and/or solvate thereof to be administered depends on the specific case and, as is usual, has to be adapted by the physician according to the customary rules and procedures to the individual circumstances in order to achieve an optimum effect. It depends, for example, on the nature and the severity of the disorder to be treated, the sex, age, weight and individual responsiveness of the human or animal patient, on the efficacy and duration of action of the compound used, on whether the treatment is for the therapy of a acute or chronic disease or prophylactic, or on whether other active compounds are administered in addition to a compound of the formula I. In general, a daily dose from about 0.01 mg/kg to about 100 mg/kg, or from about 0.1 mg/kg to about 10 mg/kg, or from about 0.3 mg/kg to about 5 mg/kg (in each case mg per kg of bodyweight), for example, is appropriate for administration to an adult weighing about 75 kg in order to obtain the desired results. The daily dose can be administered in a single dose or, in particular when larger amounts are administered, divided into several, for example two, three or four, individual doses. The administration can also be carried out continuously, for example by continuous infusion or injection. Depending on the individual behavior in a specific case, it may be necessary to deviate upward or downward from the indicated dosages.

The compounds of the formula I can also be used for other purposes than those indicated in the foregoing. Non-limiting examples include the use as diagnostics, for example the use in methods for determining the activity of Edg-1 receptors in biological samples, the use as biochemical tools, and the use as intermediates for the preparation of further compounds, for example further pharmacologically active compounds.

The following examples illustrate the invention.

When example compounds containing a basic group were purified by preparative high pressure liquid chromatography (HPLC) on reversed phase (RP) column material and, as customary, the eluent was a gradient mixture of water and acetonitrile containing trifluoroacetic acid (TFA), they were in part obtained in the form of their acid addition salt with trifluoroacetic acid, depending on the details of the workup such as evaporation or lyophilization conditions. In the names of the example compounds and their structural formulae any such contained trifluoroacetic acid is not specified.

The prepared compounds were in general characterized by spectroscopic data and chromatographic data, in particular mass spectra (MS) and HPLC retention times (Rt; in min) which were obtained by combined analytical HPLC/MS characterization (LC/MS), and/or nuclear magnetic resonance (NMR) spectra. In the NMR characterization, the chemical shift δ (in ppm), the number of hydrogen atoms and the multiplicity (s=singlet, d=doublet, dd=double doublet, t=triplet, dt=double triplet, q=quartet, m=multiplet; br=broad) of the peaks is given. In the MS characterization, in general the mass number (m/z) of the peak of the molecular ion M, e.g. M$^+$, or of a related ion such as the ion M+1, e.g. [M+1]$^+$, i.e. the protonated molecular ion [M+H]$^+$, which was formed depending on the ionization method used, is given. Generally, the ionization method was electrospray ionization (ESI). The LC/MS conditions used were as follows.

Method LC1

Column: UPLC BEH C18, 50×2.1 mm, 1.7 μm; flow: 0.9 ml/min; eluent A: acetonitrile+0.08% formic acid; eluent B: water+0.1% formic acid; gradient: from 5% A+95% B to 95% A+5% B in 1.1 min, then 95% A+5% B for 0.6 min; MS ionization method: ESI$^+$

EXAMPLE 1

[2,6-Dimethyl-4-(5-phenoxy-oxazolo[5,4-d]pyrimidin-2-yl)-phenoxy]-acetic acid

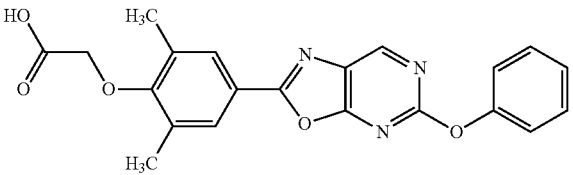 [SMILES: Cc1cc(-c2nc3cnc(Oc4ccccc4)nc3o2)cc(C)c1OCC(=O)O]

(a) N-(2,4-Dichloro-pyrimidin-5-yl)-4-methoxy-3,5-dimethyl-benzamide

A solution of 3.2 g of 5-amino-2,4-dichloro-pyrimidine in 50 ml of ethyl acetate was added to a mixture of 25 ml of a saturated aqueous sodium hydrogencarbonate solution and 25 ml of water. A solution of 4.9 g of 3,5-dimethyl-4-methoxy-benzoyl chloride was added at room temperature over a period of 15 min. The mixture was mixed intensively for 4 h. Then the layers were separated and the aqueous layer was extracted twice with ethyl acetate. After drying over sodium sulfate and filtration, the solvent was removed in vacuo to give 7.54 g of raw product. The raw product was triturated with 25 ml of isopropanol. After filtration and washing with 10 ml of isopropanol 2.74 g of the title compound was obtained as a white solid.

(b) 5-Chloro-2-(4-methoxy-3,5-dimethyl-phenyl)-oxazolo[5,4-d]pyrimidine

A solution of 2.74 g of N-(2,4-dichloro-pyrimidin-5-yl)-4-methoxy-3,5-dimethyl-benzamide and 3.2 ml of N,N-diisopropylethylamine in 17 ml of acetonitrile was split into two batches which were each heated for 1 h to 160° C. in a microwave reactor. The batches were then recombined and the precipitate was isolated by filtration to give 600 mg of the title compound as a dark but quite pure solid (600 mg). The solvents of the mother liquor were removed in vacuo and the residue was subjected to silica gel chromatography (heptane/ethyl acetate gradient) to give another 600 mg of the title compound as a pale yellow solid.

(c) 4-(5-Chloro-oxazolo[5,4-d]pyrimidin-2-yl)-2,6-dimethyl-phenol

A solution of 1.2 g of 5-chloro-2-(4-methoxy-3,5-dimethyl-phenyl)-oxazolo[5,4-d]pyrimidine in 42 ml of dichloromethane was cooled to 0° C., and over a period of 10 min 10 ml of a 1 M solution of boron tribromide in dichloromethane was added. The mixture was stirred at 0° C. for 1 h, and then another 3 ml of a 1 M solution of boron tribromide in dichloromethane were added. After stirring for another 1 h, 20 ml of a saturated aqueous solution of sodium hydrogencarboante were added slowly. The precipitate was filtered off and washed with water to give 1 g of the title compound.

(d) [4-(5-Chloro-oxazolo[5,4-d]pyrimidin-2-yl)-2,6-dimethyl-phenoxy]-acetic acid tert-butyl ester A solution of 1 g of 4-(5-chloro-oxazolo[5,4-d]pyrimidin-2-yl)-2,6-dimethyl-phenol in 5 ml of dimethylformamide was added slowly to a suspension of 1.2 ml of tert-butyl bromoacetate and 1.3 g of potassium carbonate in 15 ml of dimethylformamide. The mixture was stirred at room temperature for 30 min and then heated to 50° C. for 4 h. After cooling, the solids were removed by filtration and the solvents were distilled off in vacuo to give 1.4 g of the crude title compound as a pale yellow solid.

(e) [2,6-Dimethyl-4-(5-phenoxy-oxazolo[5,4-d]pyrimidin-2-yl)-phenoxy]-acetic acid tert-butyl ester 19 mg of sodium hydride were added under an argon atmosphere to a solution of 38 mg of phenol in 5 ml of dimethylacetamide. After stirring for 30 min at room temperature, a solution of 156 mg of [4-(5-chloro-oxazolo[5,4-d]pyrimidin-2-yl)-2,6-dimethyl-phenoxy]-acetic acid tert-butyl ester in 3 ml of dimethylacetamide was added slowly. The mixture was allowed to stir for 1.5 h at room temperature. Upon consumption of the starting ester an aqueous solution of citric acid (100 g/l) was added until the pH was neutral. The aqueous layer was extracted twice with 15 ml ethyl acetate. The combined organic layers were dried over sodium sulfate, filtered and the solvents were removed in vacuo. The title compound was isolated by silica gel chromatography (heptane/ethyl acetate gradient). Yield: 77 mg of a white solid.

(f) [2,6-Dimethyl-4-(5-phenoxy-oxazolo[5,4-d]pyrimidin-2-yl)-phenoxy]-acetic acid A solution of 77 mg of [2,6-dimethyl-4-(5-phenoxy-oxazolo[5,4-d]pyrimidin-2-yl)-phenoxy]-acetic acid tert-butyl ester in 0.7 ml of trifluoroacetic acid was stirred at room temperature for 2 h. Then 5 ml of toluene were added and the solvents were distilled off in vacuo. The residue was triturated with 2 ml of acetonitrile, and the title compound was isolated by filtration. Yield: 26 mg of a white solid.

LC/MS (method LC1): Rt=1.24 min; m/z=392.2 [M+H]$^+$

EXAMPLE 2

(E)-3-{4-[5-(2-Fluoro-phenoxy)-oxazolo[5,4-d]pyrimidin-2-yl]-phenyl}-acrylic acid

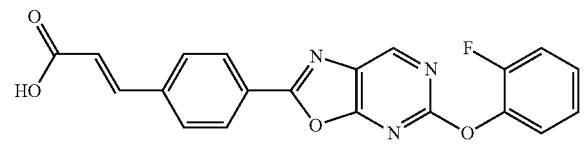 [SMILES: O=C(O)/C=C/c1ccc(-c2nc3cnc(Oc4ccccc4F)nc3o2)cc1]

(a) 2-(4-Bromo-phenyl)-5-chloro-oxazolo[5,4-d]pyrimidine

The title compound was prepared as described in example 1, steps (a) and (b), using 4-bromo benzoyl chloride in step (a).

(b) 2-(4-Bromo-phenyl)-5-(2-fluoro-phenoxy)-oxazolo[5,4-d]pyrimidine 70 mg of sodium hydride were added under argon atmosphere to a solution of 162 µl of 2-fluoro-phenol in 10 ml of dimethylacetamide. After stirring for 30 min at room temperature, a suspension of 450 mg of 2-(4-bromo-phenyl)-5-chloro-oxazolo[5,4-d]pyrimidine in 5 ml of dimethylacetamide was added slowly. The mixture was allowed to stir for 2 h at room temperature. Upon consumption of the starting oxazolo[5,4-d]pyrimidine an aqueous solution of citric acid (100 g/l) was added until the pH was neutral. The precipitate formed during addition of the citric acid solution was filtered off and washed with water to give 472 mg of the title compound.

LC/MS (method LC1): Rt=1.38 min; m/z=386.1 [M+H]$^+$

(c) (E)-3-{4-[5-(2-Fluoro-phenoxy)-oxazolo[5,4-d]pyrimidin-2-yl]-phenyl}-acrylic acid tert-butyl ester 300 mg of 2-(4-bromo-phenyl)-5-(2-fluoro-phenoxy)-oxazolo[5,4-d]pyrimidine, 36 mg of tris(dibenzylidenacetone)dipalladium(0) and 23 mg of tri-tert-butylphosphonium tetrafluoroborate were placed into a reaction vial which was closed with a septum and three times evacuated and filled with argon. The solids were dissolved in 5.5 ml of degassed 1,4-dioxane which was added with syringe. Subsequently, 0.124 ml of tert-butyl acrylate and 0.181 ml of N,N-dicyclohexyl-methylamine were added with syringe, and the mixture was heated to 120° C. in a microwave reactor for 6 h. After cooling, the mixture was diluted with 100 ml of ethyl acetate, filtrated over silica gel and concentrated in vacuo. The residue was purified by preparative HPLC. 147 mg of the title compound were obtained.

LC/MS (method LC1): Rt=1.44 min; m/z=434.14 [M+H]$^+$ (d) (E)-3-{4-[5-(2-Fluoro-phenoxy)-oxazolo[5,4-d]pyrimidin-2-yl]-phenyl}-acrylic acid A solution of 145 mg of (E)-3-{4-[5-(2-fluoro-phenoxy)-oxazolo[5,4-d]pyrimidin-2-yl]-phenyl}-acrylic acid tert-butyl ester in 2 ml of dichloromethane and 1 ml of trifluoroacetic acid was stirred at room temperature for 1.5 h. Then the mixture was concentrated in vacuo and freeze-dried. 154 mg of the title compound were obtained. LC/MS (method LC1): Rt=1.25 min; m/z=378.08 [M+H]$^+$ Analogously to the preparation of the example compounds described above, the example compounds of the formula I listed in Table 1 were prepared. In part, they were obtained in the form of their trifluoroacetic acid salt.

Analogously to the preparation of the example compounds described above, the example compounds of the formula I listed in Table 1 were prepared.

TABLE 1

Example compounds of the formula I

| Example | Name | LC/MS | m/z [M + H]$^+$ | Rt [min] |
|---|---|---|---|---|
| 3 | {4-[5-(2,4-difluoro-phenoxy)-oxazolo[5,4-d]pyrimidin-2-yl]-2,6-dimethyl-phenoxy}-acetic acid | LC1 | 428.36 | 1.29 |
| 4 | {4-[5-(2,5-difluoro-phenoxy)-oxazolo[5,4-d]pyrimidin-2-yl]-2,6-dimethyl-phenoxy}-acetic acid | LC1 | 428.32 | 1.30 |
| 5 | {4-[5-(2-fluoro-4-methyl-phenoxy)-oxazolo[5,4-d]pyrimidin-2-yl]-2,6-dimethyl-phenoxy}-acetic acid | LC1 | 424.28 | 1.30 |
| 6 | {4-[5-(2-fluoro-phenoxy)-oxazolo[5,4-d]pyrimidin-2-yl]-2,6-dimethyl-phenoxy}-acetic acid | LC1 | 410.21 | 1.26 |
| 7 | 2-{4-[5-(2-fluoro-phenoxy)-oxazolo[5,4-d]pyrimidin-2-yl]-2,6-dimethyl-phenoxy}-propionic acid | LC1 | 424.24 | 1.27 |
| 8 | {4-[5-(3-chloro-phenoxy)-oxazolo[5,4-d]pyrimidin-2-yl]-2,6-dimethyl-phenoxy}-acetic acid | LC1 | 426.18 | 1.30 |
| 9 | {4-[5-(3-fluoro-4-methyl-phenoxy)-oxazolo[5,4-d]pyrimidin-2-yl]-2,6-dimethyl-phenoxy}-acetic acid | LC1 | 424.24 | 1.29 |
| 10 | {4-[5-(5-fluoro-2-methyl-phenoxy)-oxazolo[5,4-d]pyrimidin-2-yl]-2,6-dimethyl-phenoxy}-acetic acid | LC1 | 424.31 | 1.31 |
| 11 | {4-[5-(4-chloro-phenoxy)-oxazolo[5,4-d]pyrimidin-2-yl]-2,6-dimethyl-phenoxy}-acetic acid | LC1 | 426.24 | 1.30 |
| 12 | [4-(5-cyclopentyloxy-oxazolo[5,4-d]pyrimidin-2-yl)-2,6-dimethyl-phenoxy]-acetic acid | LC1 | 384.27 | 1.30 |
| 13 | {4-[5-(2-fluoro-phenoxy)-oxazolo[5,4-d]pyrimidin-2-yl]-2-methyl-phenoxy}-acetic acid | LC1 | 396.16 | 1.26 |
| 14 | {4-[5-(2-fluoro-phenoxy)-oxazolo[5,4-d]pyrimidin-2-yl]-phenoxy}-acetic acid | LC1 | 382.11 | 1.22 |
| 15 | 2-{4-[5-(2-fluoro-phenoxy)-oxazolo[5,4-d]pyrimidin-2-yl]-phenoxy}-2-methyl-propionic acid | LC1 | 410.16 | 1.29 |
| 16 | 2-{4-[5-(2-fluoro-phenoxy)-oxazolo[5,4-d]pyrimidin-2-yl]-phenoxy}-propionic acid | LC1 | 396.14 | 1.25 |
| 17 | {4-[5-(2-fluoro-phenoxy)-oxazolo[5,4-d]pyrimidin-2-yl]-2-trifluoromethyl-phenoxy}-acetic acid | LC1 | 450.13 | 1.29 |

Determination of the Pharmacological Activity

A) GTP-γ-S Assay Using Human Edg-1 Receptors

In order to determine the Edg-1 receptor activation by the compounds of the invention, a GTP-γ-S (guanosine 5'-[γ-thio]triphosphate) assay for G-protein coupled receptor binding based on the scintillation proximity assay principle was used, employing a cell membrane preparation from a CHO Flp-In cell line which constitutively overexpresses the human Edg-1 receptor.

(a) Cell Line Generation

The Flp-In™ expression system (Invitrogen, cat. no. K6010-01) allows the generation of stable mammalian cell lines into which the gene of interest has been integrated through homologous recombination at a specific genomic location called Flp Recombination Target (FRT) site by means of a Flp recombinase encoded by the pOG44 expression plasmid. The integration of the pcDNA5/FRT expression construct into the Flp-In host cell line genome results in the transcription of the gene of interest. The stably transfected cells become hygromycin-resistant.

One day prior to transfection, 200 000 Flp-In-CHO cells were seeded in Ham F-12 medium (Invitrogen, cat. no. 31765) supplemented with 10% fetal calf serum (FCS; Perbio Science, cat. no. SH30068.03) in a 6-well plate and incubated at 37° C./5% $CO_2$ overnight. Using the FuGENE® 6 transfection reagent (Roche, cat. no. 11988387001), cells were cotransfected with the Flp recombinase expression plasmid pOG44 and a modified plasmid additionally containing the edg-1 gene (accession no. NM_001400) termed as pcDNA5-FRT-TO_nFLAG_DEST-EDG-1 with a 9:1 ratio. To obtain the modified pcDNA5-FRT-TO_nFLAG_DEST plasmid, the Invitrogen plasmid pcDNA5/FRT/TO (Invitrogen, cat. no. V6520-20) was adapted to the Gateway® (Invitrogen) cloning system by inserting a Gateway cassette containing attR recombination sites flanking a ccdB gene and a chloramphenicol-resistance gene (Gateway conversion system, Invitrogen, cat. no. 11828-029). In addition a FLAG tag epitope was added before the 5' att recombination site to allow recombinant expression of N-terminally FLAG-tagged proteins.

For the transfection of one well, 1.08 μg of pOG44 and 0.12 μg of pcDNA5-FRT-TO_nFLAG_DEST-EDG-1 were mixed to 100 μl of serum-free Ham F-12 medium containing 6 μl of FuGENE® 6 transfection reagent. After 20 min of incubation, the transfection reagent/DNA complex was distributed dropwise on the cells. The cells were incubated for 24 h at 37° C. Then the cells from 3 wells each were transferred to a T75 flask (Greiner Cellstar®, cat. no. 658175) containing Ham F-12 medium supplemented with 10% of FCS but without antibiotic and were incubated another 24 h. 48 h after transfection, the medium was replaced by selection medium (Ham F-12 supplemented with 10% of FCS and 300 μg/ml of hygromycin B (Invitrogen, cat. no. 10687-010)). The medium was exchanged every 2 to 3 days until a resistant population of cells had grown. Cells were several times splitted and seeded into a new flask so that the cells did not reach more than 25% of confluency. After 2 weeks of selection, the cells were transferred into T175 flasks (Greiner Cellstar®, cat. no. 660175) and cultivated for batch production. Cells were harvested from the culture flasks by short treatment (2 to 5 min) with Accutase (PAA, cat. no. L11-007), resuspended in selection medium (see above) and centrifuged at 200×g for 5 min. Cells were resuspended in a mixture of 90% of FCS and 10% of dimethylsulfoxide and stored frozen in liquid nitrogen.

(b) Membrane Preparation

A membrane preparation was obtained by standard methods from the afore-described CHO Flp-In cell line constitutively overexpressing the human Edg-1 receptor. Briefly, the cryopreserved cells were taken in culture and grown until confluency in T175 cell culture flasks (Becton Dickinson, cat. no. 35 5001). Cell culture was stopped by washing with calcium-free phosphate-buffered saline (PBS; Gibco, cat. no. 14190), and cells were harvested with a rubber-policeman in 4° C. cold and calcium-free PBS supplemented with a protease inhibitor cocktail (complete protease inhibitor; Roche, cat. no. 1697498; 1 tablet per 50 ml) and subsequently centrifuged at 4° C. for 15 min at 1100×g (Heraeus Minifuge T). For cell lysis, the pellet was resuspended in a 4° C. cold hypotonic buffer consisting of 5 mM HEPES (Sigma-Aldrich, cat. no. H-0981), 1 mM EDTA (disodium salt; Merck, cat. No. 8418) supplemented with protease inhibitor cocktail (as above) in which cells were stored for another 15 min on ice. After lysis, cells were centrifuged at 4° C. for 10 min at 400×g (Heraeus Minifuge T). The pellet was disrupted in a Dounce homogenizer, diluted with the supernatant of the previous centrifugation and subsequently centrifuged at 4° C. for 10 min at 500×g (Heraeus Minifuge T) in order to separate nuclei and still intact cells from the membranes mainly present in the supernatant. The supernatant was then diluted in hypotonic buffer and centrifuged (Beckmann, Avanti J251) at approximately 18600×g for 2 h at 4° C. After centrifugation, the membrane pellet was resuspended in a storing buffer consisting of 20 mM HEPES; 150 mM NaCl (Merck, cat. no. 6400), 1 mM EDTA (as above) supplemented with protease inhibitor cocktail (as above). The membrane preparation was aliquoted and stored at −80° C. Protein concentration of the membrane preparation was determined in a sample by means of a commercial protein assay (Bio-Rad, DC Protein Assay, cat. nos. 500-0113, 500-0114, 500-0115).

(c) GTP-γ-S Assay

The Edg-1 membrane preparation obtained in (b) was employed in a commercially available scintillation proximity assay (SPA) kit for G-protein coupled receptor binding from Amersham Biosciences/GE Healthcare (code RPNQ0210), in which ligand-induced binding of $^{35}$S-radiolabeled GTP-γ-S to the receptor-containing membrane, which is bound to scintillation beads, stimulates the emission of light and allows to quantify the in vitro activity of the Edg-1 agonistic compound. The assay was performed on a 96-well plate scale substantially according to the manufacturer's instructions. Before start of the experiments, scintillation beads were suspended in a reconstitution buffer consisting of Tris-HCl (pH 7.4) supplemented with 0.1% (w/v) sodium azide and subsequently diluted on ice with assay buffer (consisting of 20 mM HEPES, 100 mM NaCl, 1 mM EDTA (as above), 1 mM dithiothreitol (DTT), adjusted to pH 7.4) to a final bead concentration of 30 mg/ml.

Wells were charged with 10 μl of the specified assay buffer, 10 μl of a 100 μM guanosine diphosphate (GDP) solution, and 10 μl of a solution of the test compound in assay buffer/dimethylsulfoxide resulting in a final concentration of the test compound of 10 μM. For the high controls, 10 μl of a solution of sphingosine-1-phosphate (S1P; Sigma, cat. no. S-9666), resulting in a final S1P concentration of 10 μM, and for the low controls 10 μl of assay buffer, was added into respective wells instead of the solution of the test compound. All wells contained equivalent amounts of dimethylsulfoxide. Then 10 μl of a [$^{35}$S]GTP-γ-S solution (4 nM) and the Edg-1 membrane preparation obtained in (b) (15 μg membrane proteins in 100 μl of assay buffer) was added to each well. After incubation of the plates at room temperature for min, 50 μl of the specified scintillation bead suspension (30 mg/ml) was added. After a further incubation period of 45 min at room temperature, plates were centrifuged for 10 min at 500×g. Quantification of [$^{35}$S]GTP-γ-S binding and thus receptor activation was measured by means of a beta counter (MicroBeta, Wallac) over 1 min. Values were background-corrected by subtraction of the respective low control. All measurements were made in triplicate. The receptor activation by the test compound is expressed in percent of the respective high control (10 μM S1P; regarded as 100% activation). In Table 2 activations observed with example compounds at 10 μM are listed.

TABLE 2

| Edg-1 receptor activation by example compounds at 10 µM in percent of the activation by 10 µM S1P | |
|---|---|
| Example | % Activation |
| 1 | 116 |
| 2 | 83 |
| 3 | 95 |
| 4 | 103 |
| 5 | 101 |
| 6 | 110 |
| 7 | 84 |
| 8 | 74 |
| 9 | 87 |
| 10 | 112 |
| 11 | 105 |
| 12 | 46 |

The invention claimed is:

1. A compound of the formula I, in any of its stereoisomeric forms, or a mixture of stereoisomeric forms in any ratio, or a physiologically acceptable salt thereof, or a physiologically acceptable solvate of any of them,

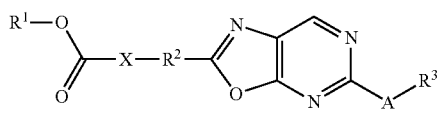

wherein

A is chosen from NH, O and S;

X is chosen from $(C_1-C_6)$-alkanediyl, $(C_2-C_6)$-alkenediyl, $(C_2-C_6)$-alkynediyl, $(C_3-C_7)$-cycloalkanediyl and $(C_1-C_6)$-alkanediyl-oxy, which all are optionally substituted by one or more identical or different substituents chosen from fluorine and hydroxy, wherein the oxygen atom of the $(C_1-C_6)$-alkanediyl-oxy group is bonded to the group $R^2$;

$R^1$ is chosen from hydrogen, $(C_1-C_4)$-alkyl and $(C_3-C_7)$-cycloalkyl-$C_zH_{2z}$—, wherein z is chosen from 0, 1 and 2;

$R^2$ is chosen from phenylene and a divalent residue of an aromatic, 5-membered to 6-membered monocyclic heterocycle which comprises 1, 2 or 3 identical or different ring heteroatoms chosen from N, O and S, wherein one of the ring nitrogen atoms can carry a hydrogen atom or a substituent $R^{21}$, and wherein the phenylene and divalent residue of an aromatic heterocycle are optionally substituted on one or more ring carbon atoms by identical or different substituents $R^{22}$;

$R^3$ is chosen from $(C_1-C_6)$-alkyl, $(C_2-C_6)$-alkenyl, $(C_2-C_6)$-alkynyl, $(C_3-C_7)$-cycloalkyl-$C_uH_{2u}$— and Het-$C_vH_{2v}$—, wherein u and v are chosen from 1 and 2, or $R^3$ is a residue of a saturated or unsaturated, 3-membered to 10-membered, monocyclic or bicyclic ring which comprises 0, 1, 2, 3 or 4 identical or different ring heteroatoms chosen from N, O and S, wherein one or two of the ring nitrogen atoms can carry a hydrogen atom or a $(C_1-C_4)$-alkyl substituent and one or two of the ring sulfur atoms can carry one or two oxo groups, and wherein the residue of a ring is optionally substituted on one or more ring carbon atoms by identical or different substituents $R^{31}$;

$R^{21}$ is chosen from $(C_1-C_4)$-alkyl, $(C_3-C_7)$-cycloalkyl-$C_wH_{2w}$— and oxy, wherein w is chosen from 0, 1 and 2;

$R^{22}$ is chosen from halogen, hydroxy, $(C_1-C_4)$-alkyl-, $(C_1-C_4)$-alkyloxy, $(C_1-C_4)$-alkyl-$S(O)_m$—, amino, nitro, cyano, hydroxycarbonyl, $(C_1-C_4)$-alkyloxycarbonyl, aminocarbonyl and aminosulfonyl;

$R^{31}$ is chosen from halogen, $(C_1-C_4)$-alkyl, $(C_3-C_7)$-cycloalkyl, hydroxy, $(C_1-C_4)$-alkyloxy, oxo, $(C_1-C_4)$-alkyl-$S(O)_m$—, amino, $(C_1-C_4)$-alkylamino, di$((C_1-C_4)$-alkyl)amino, $(C_1-C_4)$-alkylcarbonylamino, $(C_1-C_4)$-alkylsulfonylamino, nitro, cyano, $(C_1-C_4)$-alkylcarbonyl, aminosulfonyl, $(C_1-C_4)$-alkylaminosulfonyl and di$((C_1-C_4)$-alkyl)aminosulfonyl;

Het is a residue of a saturated, 4-membered to 7-membered, monocyclic heterocycle which comprises 1 or 2 identical or different ring heteroatoms chosen from N, O and S and which is bonded via a ring carbon atom, wherein the residue of a heterocycle is optionally substituted by one or more identical or different substituents chosen from fluorine and $(C_1-C_4)$-alkyl;

m is chosen from 0, 1 and 2, wherein all numbers m are independent of each other;

wherein all cycloalkyl and cycloalkanediyl groups, independently of each other and independently of any other substituents, are optionally substituted by one or more identical or different substituents chosen from fluorine and $(C_1-C_4)$-alkyl;

wherein all alkyl, alkanediyl, $C_uH_{2u}$, $C_vH_{2v}$, $C_wH_{2w}$, $C_zH_{2z}$, alkenyl, alkenediyl, alkynyl and alkynediyl groups, independently of each other and independently of any other substituents, are optionally substituted by one or more fluorine substituents.

2. A compound of the formula I, in any of its stereoisomeric forms, or a mixture of stereoisomeric forms in any ratio, or a physiologically acceptable salt thereof, or a physiologically acceptable solvate of any of them, as claimed in claim 1, wherein A is chosen from O and S.

3. A compound of the formula I, in any of its stereoisomeric forms, or a mixture of stereoisomeric forms in any ratio, or a physiologically acceptable salt thereof, or a physiologically acceptable solvate of any of them, as claimed in claim 1, wherein X is chosen from $(C_1-C_6)$-alkanediyl, $(C_2-C_6)$-alkenediyl and $(C_1-C_6)$-alkanediyl-oxy.

4. A compound of the formula I, in any of its stereoisomeric forms, or a mixture of stereoisomeric forms in any ratio, or a physiologically acceptable salt thereof, or a physiologically acceptable solvate of any of them, as claimed in claim 1, wherein $R^2$ is chosen from phenylene and pyridinediyl, wherein the phenylene and the pyridinediyl are optionally substituted on one or more ring carbon atoms by identical or different substituents $R^{22}$.

5. A compound of the formula I, in any of its stereoisomeric forms, or a mixture of stereoisomeric forms in any ratio, or a physiologically acceptable salt thereof, or a physiologically acceptable solvate of any of them, as claimed in claim 1, wherein $R^3$ is chosen from $(C_1-C_6)$-alkyl, $(C_3-C_7)$-cycloalkyl-$C_uH_{2u}$— and Het-$C_vH_{2v}$—, wherein u and v are chosen from 1 and 2, or $R^3$ is a residue of a saturated or unsaturated, 3-membered to 10-membered, monocyclic or bicyclic ring which comprises 0, 1 or 2 identical or different ring heteroatoms chosen from N, O and S, wherein one or two of the ring nitrogen atoms can carry a hydrogen atom or a $(C_1-C_4)$-alkyl substituent and one of the ring sulfur atoms can carry one or two oxo groups, and wherein the residue of a ring is optionally substituted on one or more ring carbon atoms by identical or different substituents $R^{31}$;

Het is a residue of a saturated, 4-membered to 6-membered, monocyclic heterocycle which comprises 1 ring heteroatom chosen from N, O and S and which is bonded via a ring carbon atom, wherein the residue of a heterocycle is optionally substituted by one or more identical or different substituents chosen from fluorine and ($C_1$-$C_4$)-alkyl.

6. A compound of the formula I, in any of its stereoisomeric forms, or a mixture of stereoisomeric forms in any ratio, or a physiologically acceptable salt thereof, or a physiologically acceptable solvate of any of them, as claimed in claim 1, wherein A is chosen from O and S;
X is chosen from ($C_1$-$C_6$)-alkanediyl, ($C_2$-$C_6$)-alkenediyl and ($C_1$-$C_6$)-alkanediyl-oxy;
$R^2$ is chosen from phenylene and pyridinediyl, wherein the phenylene and the pyridinediyl are optionally substituted on one or more ring carbon atoms by identical or different substituents $R^{22}$;
$R^3$ is chosen from ($C_1$-$C_6$)-alkyl, ($C_3$-$C_7$)-cycloalkyl-$C_uH_{2u}$— and Het-$C_vH_{2v}$—, wherein u and v are chosen from 1 and 2, or $R^3$ is a residue of a saturated or unsaturated, 3-membered to 10-membered, monocyclic or bicyclic ring which comprises 0, 1 or 2 identical or different ring heteroatoms chosen from N, O and S, wherein one or two of the ring nitrogen atoms can carry a hydrogen atom or a ($C_1$-$C_4$)-alkyl substituent and one of the ring sulfur atoms can carry one or two oxo groups, and wherein the residue of a ring is optionally substituted on one or more ring carbon atoms by identical or different substituents $R^{31}$;
Het is a residue of a saturated, 4-membered to 6-membered, monocyclic heterocycle which comprises 1 ring heteroatom chosen from N, O and S and which is bonded via a ring carbon atom, wherein the residue of a heterocycle is optionally substituted by one or more identical or different substituents chosen from fluorine and ($C_1$-$C_4$)-alkyl.

7. A compound of the formula I, in any of its stereoisomeric forms, or a mixture of stereoisomeric forms in any ratio, or a physiologically acceptable salt thereof, or a physiologically acceptable solvate of any of them, as claimed in claim 1, wherein A is O.

8. A compound of the formula I, in any of its stereoisomeric forms, or a mixture of stereoisomeric forms in any ratio, or a physiologically acceptable salt thereof, or a physiologically acceptable solvate of any of them, as claimed in claim 1, wherein A is O;
X is chosen from ($C_1$-$C_6$)-alkanediyl and ($C_1$-$C_6$)-alkanediyl-oxy;
$R^1$ is chosen from hydrogen and ($C_1$-$C_6$)-alkyl;
$R^2$ is phenylene which is optionally substituted on one or more ring carbon atoms by identical or different substituents $R^{22}$;
$R^3$ is chosen from ($C_1$-$C_6$)-alkyl, ($C_3$-$C_7$)-cycloalkyl-$C_uH_{2u}$— and Het-$C_vH_{2v}$—, wherein u and v are chosen from 1 and 2, or $R^3$ is a residue of a saturated or unsaturated, 3-membered to 7-membered, monocyclic or bicyclic ring which comprises 0, 1 or 2 identical or different ring heteroatoms chosen from N, O and S, wherein one or two of the ring nitrogen atoms can carry a hydrogen atom or a ($C_1$-$C_4$)-alkyl substituent and one of the ring sulfur atoms can carry one or two oxo groups, and wherein the residue of a ring is optionally substituted on one or more ring carbon atoms by identical or different substituents $R^{31}$;
$R^{22}$ is chosen from halogen, hydroxy, ($C_1$-$C_4$)-alkyl- and ($C_1$-$C_4$)-alkyloxy;
$R^{31}$ is chosen from halogen, ($C_1$-$C_4$)-alkyl, ($C_3$-$C_7$)-cycloalkyl, hydroxy and ($C_1$-$C_4$)-alkyloxy;
Het is a residue of a saturated, 4-membered to 6-membered, monocyclic heterocycle which comprises 1 ring heteroatom chosen from O and S and which is bonded via a ring carbon atom, wherein the residue of a heterocycle is optionally substituted by one or more identical or different substituents chosen from fluorine and ($C_1$-$C_4$)-alkyl;
wherein all cycloalkyl groups, independently of each other and independently of any other substituents, are optionally substituted by one or more identical or different substituents chosen from fluorine and ($C_1$-$C_4$)-alkyl;
wherein all alkyl, alkanediyl, $C_uH_{2u}$ and $C_vH_{2v}$ groups, independently of each other and independently of any other substituents, are optionally substituted by one or more fluorine substituents.

9. A compound of the formula I, in any of its stereoisomeric forms, or a mixture of stereoisomeric forms in any ratio, or a physiologically acceptable salt thereof, or a physiologically acceptable solvate of any of them, as claimed in claim 1, wherein A is O;
X is chosen from ($C_1$-$C_6$)-alkanediyl and ($C_1$-$C_6$)-alkanediyl-oxy;
$R^1$ is chosen from hydrogen and ($C_1$-$C_4$)-alkyl;
$R^2$ is phenylene which is optionally substituted on one or more ring carbon atoms by identical or different substituents $R^{22}$;
$R^3$ is a residue of a saturated or unsaturated, 3-membered to 7-membered, monocyclic ring which comprises 0 or 1 ring heteroatom chosen from N, O and S, wherein a ring nitrogen atom can carry a hydrogen atom or a ($C_1$-$C_4$)-alkyl substituent and a ring sulfur atom can carry one or two oxo groups, and wherein the residue of a ring is optionally substituted on one or more ring carbon atoms by identical or different substituents $R^{31}$;
$R^{22}$ is chosen from halogen, hydroxy, ($C_1$-$C_4$)-alkyl- and ($C_1$-$C_4$)-alkyloxy;
$R^{31}$ is chosen from halogen, ($C_1$-$C_4$)-alkyl, ($C_3$-$C_7$)-cycloalkyl, hydroxy and ($C_1$-$C_4$)-alkyloxy;
wherein all cycloalkyl groups, independently of each other and independently of any other substituents, are optionally substituted by one or more identical or different substituents chosen from fluorine and ($C_1$-$C_4$)-alkyl;
wherein all alkyl and alkanediyl groups, independently of each other and independently of any other substituents, are optionally substituted by one or more fluorine substituents.

10. A compound of the formula I, or a physiologically acceptable salt thereof, or a physiologically acceptable solvate of any of them, as claimed in claim 1, chosen from
[2,6-dimethyl-4-(5-phenoxy-oxazolo[5,4-d]pyrimidin-2-yl)-phenoxy]-acetic acid,
(E)-3-{4-[5-(2-fluoro-phenoxy)-oxazolo[5,4-d]pyrimidin-2-yl]-phenyl}-acrylic acid,
{4-[5-(2,4-difluoro-phenoxy)-oxazolo[5,4-d]pyrimidin-2-yl]-2,6-dimethyl-phenoxy}-acetic acid,
{4-[5-(2,5-difluoro-phenoxy)-oxazolo[5,4-d]pyrimidin-2-yl]-2,6-dimethyl-phenoxy}-acetic acid,
{4-[5-(2-fluoro-4-methyl-phenoxy)-oxazolo[5,4-d]pyrimidin-2-yl]-2,6-dimethyl-phenoxy}-acetic acid,
{4-[5-(2-fluoro-phenoxy)-oxazolo[5,4-d]pyrimidin-2-yl]-2,6-dimethyl-phenoxy}-acetic acid,
2-{4-[5-(2-fluoro-phenoxy)-oxazolo[5,4-d]pyrimidin-2-yl]-2,6-dimethyl-phenoxy}-propionic acid, {4-[5-(3-chloro-phenoxy)-oxazolo[5,4-d]pyrimidin-2-yl]-2,6-dimethyl-phenoxy}-acetic acid, {4-[5-(3-fluoro-4-methyl-phenoxy)-oxazolo[5,4-d]pyrimidin-2-yl]-2,6-dimethyl-phenoxy}-acetic acid, {4-[5-(5-fluoro-2-methyl-phenoxy)-oxazolo[5,4-d]pyrimidin-2-yl]-2,6-dimethyl-phenoxy}-acetic acid, and {4-[5-(4-chloro-phenoxy)-oxazolo[5,4-d]pyrimidin-2-yl]-2,6-dimethyl-phenoxy}-acetic acid.

11. A compound of the formula I or a physiologically acceptable salt thereof, or a physiologically acceptable solvate of such a compound or of such a salt, as claimed in claim 1, chosen from {4-[5-(2-fluoro-4-methyl-phenoxy)-oxazolo[5,4-d]pyrimidin-2-yl]-2,6-dimethyl-phenoxy}-acetic acid, {4-[5-(2-fluoro-phenoxy)-oxazolo[5,4-d]pyrimidin-2-yl]-2,6-dimethyl-phenoxy}-acetic acid, {4-[5-(3-chloro-phenoxy)-oxazolo[5,4-d]pyrimidin-2-yl]-2,6-dimethyl-phenoxy}-acetic acid, {4-[5-(3-fluoro-4-methyl-phenoxy)-oxazolo[5,4-d]pyrimidin-2-yl]-2,6-dimethyl-phenoxy}-acetic acid, {4-[5-(5-fluoro-2-methyl-phenoxy)-oxazolo[5,4-d]pyrimidin-2-yl]-2,6-dimethyl-phenoxy}-acetic acid, and {4-[5-(4-chloro-phenoxy)-oxazolo[5,4-d]pyrimidin-2-yl]-2,6-dimethyl-phenoxy}-acetic acid.

12. A pharmaceutical composition, comprising at least one compound of the formula I as claimed in claim 1 or a physiologically acceptable salt thereof, or a physiologically acceptable solvate of any of them, and a pharmaceutically acceptable carrier.

13. A process for the preparation of a compound of the formula I as claimed in claim 1, comprising reacting a compound of the formula II with a compound of the formula III,

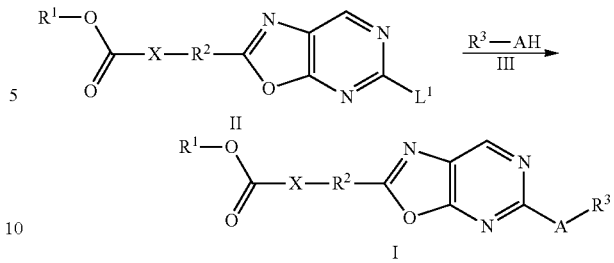

wherein the groups A, X, $R^1$, $R^2$ and $R^3$ in the compounds of the formulae II and III are defined as in the compounds of the formula I and additionally functional groups can be present in protected form or in the form of a precursor group, and the group $L^1$ is a halogen atom or a group of the formula —S(O)-Alk or —S(O)$_2$-Alk wherein Alk is ($C_1$-$C_4$)-alkyl.

14. A method of treating wound healing disorders in a patient in need thereof comprising administering to said patient a therapeutically effective amount of the pharmaceutical composition of claim 12.

15. A method of wound healing in a patient in need thereof comprising administering to said patient a therapeutically effective amount of the pharmaceutical composition of claim 12.

16. A method of wound healing in diabetics in a patient in need thereof comprising administering to said patient a therapeutically effective amount of the pharmaceutical composition of claim 12.

17. A method of treating diabetic foot syndrome in a patient in need thereof comprising administering to said patient a therapeutically effective amount of the pharmaceutical composition of claim 12.

* * * * *